US007524669B2

(12) United States Patent
Rosen et al.

(10) Patent No.: US 7,524,669 B2
(45) Date of Patent: Apr. 28, 2009

(54) **TRANSGENIC *SACCHAROMYCES CEREVISIAE* AND METHOD FOR BIOREMEDIATION**

(75) Inventors: Barry Rosen, Detroit, MI (US); Mallika Ghosh, Manchester, CT (US)

(73) Assignee: Wayne State University, Detroit, MI (US)

( * ) Notice: Subject to any disclaimer, the term of this patent is extended or adjusted under 35 U.S.C. 154(b) by 177 days.

(21) Appl. No.: 10/967,652

(22) Filed: Oct. 18, 2004

(65) Prior Publication Data

US 2005/0260739 A1 Nov. 24, 2005

Related U.S. Application Data

(63) Continuation of application No. PCT/US03/11673, filed on Apr. 16, 2003.

(60) Provisional application No. 60/373,037, filed on Apr. 16, 2002.

(51) Int. Cl.
*C12N 1/19* (2006.01)
*A62D 3/02* (2007.01)
*C12M 3/00* (2006.01)

(52) U.S. Cl. .............................. 435/254.21; 435/262.5; 435/289.1

(58) Field of Classification Search ....................... None
See application file for complete search history.

(56) References Cited

U.S. PATENT DOCUMENTS 6,166,290 A 12/2000 Rea et al.

OTHER PUBLICATIONS

"Arsenic in drinking water", *EPA Office of Water*, 5 pgs.

Adelman, J P., et al., "In vitro deletional mutagenesis for bacterial production of the 20,000-dalton form of human pituitary growth hormone", *DNA*, 2(3), (1983), 183-193.

Bobrowicz, P., et al., "Isolation of three contiguous genes, *ACR1*, *ACR2* and *ACR3*, involved in resistance to arsenic compounds in the yeast *Saccharomyces cerevisiae", Yeast*, 13(9), (1997),819-828.

Bun-Ya, M., et al., "Two new genes, PHO86 and PHO87, involved in inorganic phosphate uptake in *Saccharomyces cerevisiae", Abstract, Curr. Genet.*, 29(4), (1996),344-351.

Chappell, W. R., et al., "Inorganic arsenic: a need and an opportunity to improve risk assessment", *Environmental Health Perspective*, 105(10), (1997),1060-1067.

Chou, W. C., et al., "Arsenic inhibition of telomerase transcription leads to genetic instability", *Journal of Clinical Investigation*, 108(10), (2001),1541-1547.

Dey, S., et al., "An ATP-dependent As(III)-glutathione transport system in membrane vesicles of Leishmania tarentolae", *Proc Natl Acad Sci USA*, 93(5), (1996),2192-2197.

Fauman, E. B., et al., "Crystal structure of the catalytic domain of the human cell cycle control phosphatase, Cdc25A", *Chemistry and Biology*, 93(4), (1998),617-625.

Fu, D., et al., "Structure of a glycerol-conducting channel and the basis for its selectivity.", *Science*, 290(5491), (2000),481-486.

Ghosh, M, et al., "Microbial resistance mechanisms for heavy metals and . . . ", *in Heavy Metals in the Environment, ed.* Sarkar, B. (Dekker, New York)., (2000),531-548.

Ghosh, M., et al., "Pathways of As(III) Detoxification in *Saccharomyces cerevisiae", Proc. Natl. Acad. Sci., USA*, 96, Department of Biochemistry and Molecular Biology, Wayne State Univ. School of Medicine,(1999),5001-5006.

Gladysheva, T B., et al., "Properties of the arsenate reductase of plasmid R773", *Abstract, Biochemistry*, 33(23), (1994),7288-7293.

Hofmann, K., et al., "A model of Cdc25 phosphatase catalytic domain and Cdk-interaction surface based on the presence of a rhodanese homology domain", *Journal of Molecular Biology*, 282(1), (1998),195-208.

Ishibashi, K., et al., "Cloning and functional expression of a new water channel abundantly expressed in the testis permeable to water, glycerol, and urea", *Journal of Biological Chemistry*, 272(33), (1997),20782-20786.

Ji, G., et al., "Arsenate reductase of *Staphylococcus aureus* plasmid pl258", *Biochemistry*, 33(23), (1994),7294-7299.

Kuroda, M., et al., "Alternate energy coupling of ArsB, the membrane subunit of the Ars anion-translocating ATPase", *Journal of Biological Chemistry*, 272, (1997),326-331.

Li, Z., et al., "A New Pathway for Vacuolar Cadmium Sequestration in *Saccharomyces cerevisiae*: YCF1-Catalyzed Transport of Bis(glutathionato) Cadmium", *Proc. National Academy of Sciences of the USA*, 94, (1997),42-47.

Li, Z S., et al., "The yeast cadmium factor protein (YCF1) is a vacuolar glutathione S-conjugate pump", *Journal of Biological Chemistry*, 271(11), (1996),6509-6517.

Liu, Z, et al., "Arsenite transport by mammalian aquaglyceroporins AQP7 and AQP9", *Proc Natl Acad Sci U S A.*, 99(9), (2002),6053-6058.

Mukhopadhyay, Rita, et al., "Purification and Characterization of Acr2p, the *Saccharomyces cerevisiae* Arsenate Reductase", *Journal of Biological Chemistry*, 275(28), (2000),21149-21157.

Mukhopadhyay, R., et al., "*Saccharomyces cerevisiae ACR2* gene encodes an arsenate reductase", *FEMS Microbiology Letters*, 168(1), (1998),127-136.

Murata, K., et al., "Structural determinants of water permeation through aquaporin-1", *Nature*, 407(6804), (2000),599-605.

Nejsum, L N., et al., "Localization of Aquaporin-7 in Rat and Mouse Kidney Using RT-PCR, Immunoblotting, and Immunocytochemistry", *Biochemical and Biophysical Research Communications*, 277(1), (2000),164-170.

Rosen, B. P., "Transport and Detoxification Systems for Transition Metals, Heavy Metals and Metalloids in Eukaryotic and Prokaryotic Microbes", *Comparative Biochemistry and Physiology*, 133, (2002),689-693.

Sui, H., et al., "Structural basis of water-specific transport through the AQP1 water channel", *Nature*, 414(6866), (2001),872-878.

(Continued)

*Primary Examiner*—Nancy Vogel
(74) *Attorney, Agent, or Firm*—Schwegman, Lundberg & Woessner, P.A.

(57) ABSTRACT

An isolated and purified transgenic *Saccharomyces cerevisiae* yeast cell comprising a disrupted ACR3 gene and an isolated DNA sequence comprising a promoter operably linked to a nucleic acid molecule encoding yeast cadmium factor resistance protein Ycf1p, is provided, as well as uses of the transgenic yeast cell.

21 Claims, 6 Drawing Sheets

OTHER PUBLICATIONS

Szczypka, M. S., et al., "A yeast metal resistance protein similar to human cystic fibrosis transmembrane conductance regulator (CFTR) and multidrug resistance-associated protein", *J Biol Chem*., 269(36), (2004),22853-22857.

Willsky, G. R., et al., "Characterization of two genetically separable inorganic phosphate transport systems in *Escherichia coli", J Bacteriol*., 144(1), (1980),356-365.

Wysocki, R., et al., "The glycerol channel Fps1p mediates the uptake of arsenite and antimonite in *Saccharomyces cerevisiae", Molecular Microbiology*, 40(6), (2001),1391-401.

Wysocki, Robert, et al., "The *Saccharomyces cerevisiae ACR3* gene encodes a putative membrane protein involved in arsenite transport", *The Journal of Biological Chemistry*, 272(48), (1997),30061-30066.

"International Application No. PCT/US03/11673 International Preliminary Examination Report mailed Sep. 13, 2004", 5 pgs.

"International Application No. PCT/US03/11673 International Search Report mailed Sep. 4, 2003", 7 pgs.

TRANSGENIC *SACCHAROMYCES CEREVISIAE* AND METHOD FOR BIOREMEDIATION

CLAIM OF PRIORITY

This application is a continuation application filed under 35 U.S.C. § 111(a) of International Application No. PCT/US03/11673, filed on Apr. 16, 2003, which claims the benefit under 35 U.S.C. under § 119(e) to U.S. Provisional Application Ser. No. 60/373,037, filed Apr. 16, 2002, both of which are incorporated herein by reference.

STATEMENT OF GOVERNMENT RIGHTS

The invention described herein was made with government support under Grant Numbers GM55425, GM52216, AI 43428 and ES10344 awarded by the National Institutes of Health. The United States Government has certain rights in the invention.

BACKGROUND OF THE INVENTION

Arsenic contamination of drinking water poses a substantial threat to public health (Waldman, 2001). Concentrations of arsenic in groundwater in some areas are elevated as a result of erosion from local rocks. In addition, the combustion of fossil fuels and industrial effluents (arsenic is a by-product of industrial processes including semiconductor manufacturing, petroleum refining, and mining and smelting operations) contribute to arsenic contamination in drinking water. Severe health effects have been observed in populations drinking arsenic-rich water over long periods in many countries. According to the Environmental Protection Agency (EPA), international studies have linked long-term exposure to arsenic in drinking water to cancer of the bladder, lungs, skin, e.g., basal cell carcinoma, squamous cell carcinoma, kidney, nasal passages, liver and prostate (Walsh, 2001). Arsenic exposure has also been linked to numerous other deleterious effects on various organ systems of the human body, e.g., skin (hyperkeratosis of palms and soles, melanosis or depigmentation, Bowen's disease), liver (enlargement of the liver, jaundice, cirrhosis, non-cirrhotic portal hypertension), nervous system (peripheral neuropathy, hearing loss), cardiovascular system (acrocyanosis, Raynaud's phenomenon), the respiratory system as well as the endocrine system (diabetes mellitus and goiter).

On Oct. 31, 2001, the EPA announced its decision to move forward in revising the existing 50 parts per billion (ppb) standard for arsenic in drinking water by implementing a maximum contaminant level (MCL), or regulatory level, of 10 parts per billion (ppb). Water systems will have to meet this new standard by January 2006.

In water, the most common valence states of arsenic are As(V), or arsenate, which is more prevalent in aerobic surface waters and As(III), or arsenite, which is more likely to occur in anaerobic ground waters. In the pH range of 4 to 10, the predominant As (III) compound is $As(OH)_3$, which is neutral in charge, while the As (V) species are negatively charged. Removal efficiencies for As(III) are poor compared to removal As(V) by existing technologies due to the lack of negative charge. As (III) may be converted to As(V) by oxidation. Ferric chloride and potassium permanganate are effective in oxidizing As(III) to As(V). However, pre-oxidation with chlorine may create undesirable concentrations of disinfection by-products.

Coagulation/filtration (C/F), the standard treatment for remediating arsenic and other contaminants from surface water, uses iron that reacts with arsenic salts to create a solid that precipitates from the water. The type of coagulant and dosage used affects the efficiency of the process. Within either high or low pH ranges, the efficiency of C/F is significantly reduced. Moreover, this treatment system requires large settling tanks, and produces an arsenic-contaminated sludge that may need to be disposed of in a hazardous waste landfill based upon the revised EPA arsenic standard. C/F is not appropriate for most small water treatment systems due to high costs associated with the technique, as well as the need for well trained operators. In addition, there is variability in process performance of C/F treatment systems.

Another remediation technique, lime softening (LS), can provide a high percentage of arsenic removal for influent concentrations of 50 μg/L when operated within the optimum pH range of greater than 10.5. However, as with C/F, LS is not applicable for small water treatment systems due to the prohibitive costs associated with the technique. Moreover, it may be difficult to consistently meet a low-level MCL using either C/F or LS alone. Disposal of contaminated sludge generated during L/S may also present a problem Activated alumina (AA) is effective in treating water with high total dissolved solids (TDS). However, selenium, fluoride, chloride, and sulfate, if present at high levels, may compete for adsorption sites. AA is highly selective towards As(V), and this strong attraction results in regeneration problems, possibly resulting in 5 to 10 percent loss of adsorptive capacity for each run. Drawbacks to this technique also include the lack of availability of F-1 alumina. In addition, chemical handling requirements may make this process too complex and dangerous for many small systems. Moreover, AA may not be efficient in the long term, as it seems to lose significant adsorptive capacity with each regeneration cycle, and disposal of highly concentrated waste streams produced by this technique may also be problematic.

Ion exchange (IE), e.g., anion exchange, technology can effectively remove arsenic from contaminated water. However, sulfate, TDS, selenium, fluoride, and nitrate compete with arsenic for exchange and can affect run length. Suspended solids and precipitated iron can cause clogging of the IE bed. Thus, systems containing high levels of these constituents may require pretreatment. Anion exchange involves passing water with anions of arsenate through a column of resin beads containing exchangeable, innocuous ions such as chloride, resulting in an exchange that leaves the arsenate in the beads and the chloride in the water. IE will not remove uncharged compounds, which means it will not work with uncharged As(III) unless it is pre-oxidized. In addition, removing contaminants at lower levels will affect how soon the exchange column must be regenerated before breakthrough (the point at which removal levels begin to deteriorate). In addition, IE produces an arsenic-contaminated brine, the disposal of which may be problematic.

Another common water treatment approach, reverse osmosis (RO) involves pushing water through a membrane that captures contaminants. Although effective in removing contaminants to below 2 μg/l, RO is a more expensive technology than C/F and produces a brine that itself must be treated for arsenic contamination. Moreover, RO produces a larger waste stream than other treatment methods, which may make the method impractical in locales where water is scarce.

Additional methodologies currently employed for water remediation include electrodialysis reversal (EDR) and nanofiltration (NF). EDR is expected to achieve removal efficiencies of 80 percent. In one study, NF was capable of arsenic removals of over 90%, however, a recent study showed that the removal efficiency dropped significantly during pilot-scale tests where the process was operated at more realistic recoveries. With either of these techniques, water rejection (about 20-25 percent of influent) may be an issue in water-scarce regions. Moreover, EDR may not be competitive with respect to costs and process efficiency when compared with RO and NF.

In bioremediation methodology, microorganisms, both naturally occurring and/or genetically engineered, are used as agents to remove contaminants such as organic compounds, e.g., petroleum hydrocarbons, from soils and water. This technology has recently emerged as a viable remediation method (Ritter and Scarborough, 1995). Additionally, in recent years phytoremediation, the use of plants and trees to clean up contaminated soil and water, has been used to treat hazardous wastes. For example, U.S. Pat. No. 6,166,290 discusses the use of transgenic plants, i.e., plants encoding a glutathione S-conjugate (GS-X) pump, e.g., the yeast vacuolar Ycf1p pump, for the bioremediation of contaminated soils.

As there are several disadvantages associated with the remediation techniques currently employed to remove arsenic from water, there is a need for a bioremediation method that removes arsenic from contaminated water.

SUMMARY

The present invention provides an isolated and purified transgenic *Saccharomyces cerevisiae* yeast cell comprising (a) a disrupted ACR3 gene of said yeast cell, wherein the disruption results in a reduction of Acr3p activity in the transgenic *S. cerevisiae* yeast cell as compared to a corresponding wild-type *S. cerevisiae* yeast cell, and (b) an isolated DNA sequence comprising a promoter operably linked to a nucleic acid molecule encoding yeast cadmium resistance factor protein Ycf1p, wherein the transgenic *S. cerevisiae* yeast cell overexpresses Ycf1p as compared to the corresponding wild-type *S. cerevisiae* yeast cell, such that the overexpression of Ycf1p and the reduction of Acr3p activity causes the transgenic *S. cerevisiae* yeast cell to hyperaccumulate at least one heavy metal, e.g., As(V), As(III), cadmium (Cd(II)), antimony (Sb(V), Sb(III)), mercury (Hg(II)), and/or lead (Pb(II)), from an aqueous medium. A reduction of Acr3p activity can be, for example, a reduction in the ability of the transgenic *S. cerevisiae* yeast cell to extrude As(III), e.g., extrusion of As(III) from the cell back into the aqueous medium.

The expression of the ACR3 gene of the transgenic *S. cerevisiae* yeast cell can be disrupted, for example, by insertional inactivation, e.g., homologous recombination of the ACR3 gene with a heterologous DNA sequence.

Preferably, overexpression of Ycf1p in the transgenic *S. cerevisiae* yeast cell also can be induced. The transgenic *S. cerevisiae* yeast cell of the invention can further comprise an isolated vector comprising a promoter operably linked to a second nucleic acid molecule comprising the ACR2 gene, which encodes Acr2p. Such a transgenic *S. cerevisiae* yeast cell can overexpress Acr2p as compared to the corresponding wild-type *S. cerevisiae* yeast cell, so that the reduction of As(V) to As(III) in the transgenic *S. cerevisiae* yeast cell is not a rate limiting step in the detoxification of arsenic in the yeast cell.

The invention further provides a method for bioremediation of water comprising a heavy metal ion comprising (a) contacting, in the bioreactor, the water with a transgenic *S. cerevisiae* yeast of the invention, wherein the contact is effective to reduce the amount of heavy metal ion in the water; and (b) monitoring the concentration of heavy metal ion in the water before and after the contact.

Also provided is a bioreactor comprising a transgenic *S. cerevisiae* yeast of the invention.

DETAILED DESCRIPTION OF THE INVENTION

I. Definitions

Figure 1:
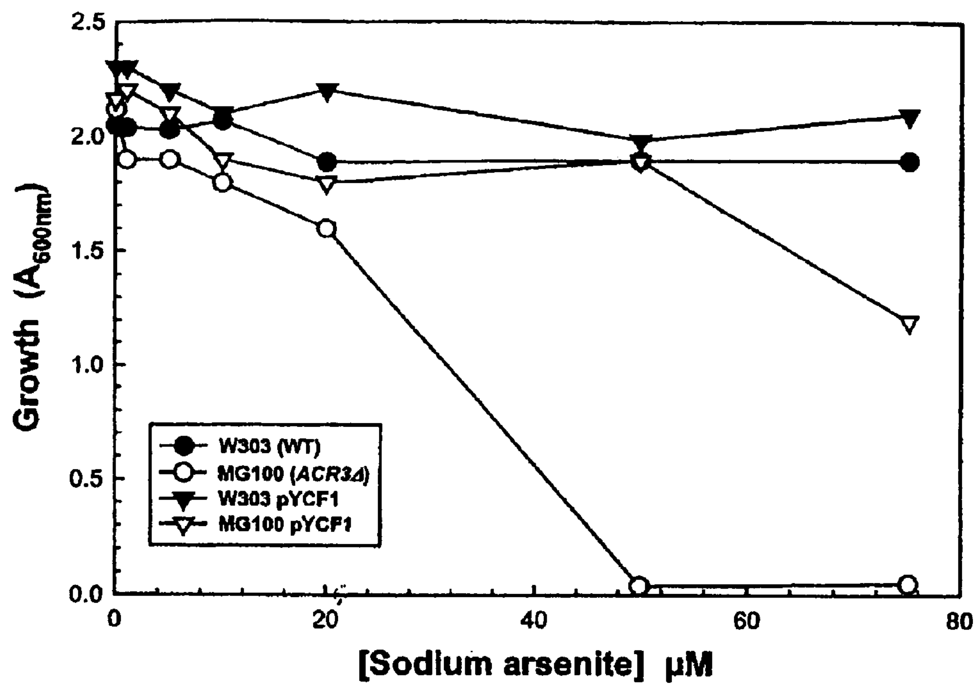
FIG. 1. Arsenite sensitivity of *S. cerevisiae* strains with disruption of both ACR3 and overexpression of YCF1. Growth was measured in liquid SD minimal medium in the presence of the indicated concentrations of sodium arsenite. Strains were closed circles: W303 (wild type ACR3); closed inverted triangles: W303 pYCF1; open circles: MG100 (ACR3Δ); open inverted triangles: MG100 pYCF1.

By "bioreactor" is meant a vessel comprising a liquid medium and a solid supporting matrix in which biological reactions are carried out by microorganisms, or the enzymes they produce, contained within the vessel itself. A wide variety of bioreactor technologies have been developed for the treatment of contaminated solids, liquids and gases (Déziel et al., 1999). The term "bioreactor" is used throughout the specification to describe any vessel or container wherein the biological isolation and/or degradation of contaminants is carried out in a controlled fashion.

Bioreactors can range from devices such as lined depressions in the ground to metal or glass containers where environmental conditions can be monitored and controlled. The essential treatment mechanism in a bioreactor is natural degradation by existing and/or added populations of microorganisms. Bioreactors for water treatment are usually fixed film or some form of activated sludge reactors. Fixed film reactors contain high surface area media that support microbial growth. Activated sludge reactors are aerated basins where microbes are mixed with the wastewater and nutrients. Bioreactors can be operated in batch or steady state flow regimes. The main objective in the design of a bioreactor is to generate an optimal environment for the desired biological process to take place on a large and economic scale.

Bioreactors can be made from an inert material such as stainless steel or glass. An exemplary bioreactor may comprise a vertical Pyrex (glass) column that is adapted with at least two inlets for medium and air at the bottom of the column and at least one outlet port at the top of the column to accommodate expunged medium and/or air. See, for example, Hamdy, et al., Biomass., 21, 189-206 (1990).

"Bioremediation" refers to any one of a number of technologies to reduce the toxicity, mobility, or amount of a contaminant rather than merely provide temporary protection for the environment via isolation and containment of the contaminant. It refers to a treatment process that uses microorganisms, e.g., naturally occurring or genetically engineered, to "detoxify", i.e., isolate or degrade, contaminants or hazardous substances into less toxic or nontoxic substances.

Two basic forms of bioremediation are the microbiological approach and the microbial ecology approach. The microbiological approach involves augmentation of a contaminated site with one or more species of contaminant-specific degrading microorganisms. The theory behind this approach is that the rate of degradation of the contaminant will be appreciably enhanced because the density of contaminant-specific degraders will have been increased artificially. Bioremediation techniques include, but are not limited to, on-site bioremediation, off-site bioremediation, in situ bioremediation, ex-situ bioremediation, slurry bioremediation, or any bioremediation method known to the art. For example, contaminated soils may be bioremediated by in-situ techniques, landfarming, composting or in slurry bioreactors. Anaerobic biodegradation may offer an effective alternative to aerobic in-situ bioremediation for some compounds.

As used herein, "disrupted gene" refers to an insertion, substitution, or deletion either in a gene of interest or in the vicinity of the gene, i.e., upstream (5') or downstream (3') of the gene, which results in the reduction of the biological activity or the loss of substantially all of the biological activity associated with the gene's product. For example, a disrupted ACR3 gene would be unable to express a protein having substantial Acr3p activity. A gene can be disrupted by any one of a number of methods known to the art, for example, by site-directed mutagenesis or homologous recombination.

"Expression" refers to the transcription and translation of an endogenous gene or a transgene in a host cell. For example, in the case of antisense constructs, expression may refer to the transcription of the antisense DNA only. In addition, expression refers to the transcription and stable accumulation of sense (mRNA) or functional RNA. Expression may also refer to the production of protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

For example, "YCF1" refers to the *Saccharomyces cerevisiae* gene that encodes vacuolar Ycf1p (Lu et al., 1996, 1997). Ycf1p (yeast cadmium resistance factor protein) is a vacuolar glutathione S-conjugate pump with a broad range of substrate specificity and confers heavy metal resistance in *S. cerevisiae* by catalyzing sequestration of metal-glutathione conjugates, such as $As(GS)_3$, in the vacuole (Ghosh et al., 1999). "ACR1" refers to the *S. cerevisiae* gene that encodes a putative transcription factor (Bobrowicz et al., 1997). "ACR2" refers to the *S. cerevisiae* gene that encodes Acr2p, an arsenate reductase enzyme that catalyzes arsenate reduction (Mukhopadhyay and Rosen, 1998), and "ACR3" refers to the *S. cerevisiae* gene that encodes the plasma membrane arsenite-efflux transporter Acr3p (404 residues, 45.8 kDa) (Rosen I; Ghosh et al., 1999).

The phrase "heavy metal" refers to heavy metals, metalloids, transition metals and their respective salts, i.e., it is meant to include at least the ionic form of cadmium (Cd(II)), arsenic (As(III), As(V)), antimony (Sb(III)), mercury (Hg (II)), or lead (Pb(II)).

"Homologous recombination" is defined as the reciprocal exchange of homologous DNA fragments anywhere along a length of homologous DNA molecules.

"Hyperaccumulation" refers to the accumulation of a compound of interest, e.g., an environmental contaminant, at very high concentrations in the cell of a yeast. For example, an arsenic hyperaccumulating yeast cell of the invention has the ability to uptake, bind, and detoxify environmental contaminants, such as metal ions, e.g., arsenic, either as As(V) or As(III), through cellular-mediated biological or biochemical means.

As used herein, the terms "isolated and/or purified" refer to in vitro preparation, isolation and/or purification of a DNA molecule, sequence or segment, so that it is not associated with the substances normally present with it in vivo.

A "mutation" refers to an insertion, deletion or substitution of one or more nucleotide bases of a nucleic acid sequence, so that the nucleic acid sequence differs from the wild-type sequence. For example, a 'point' mutation refers to an alteration in the sequence of a nucleotide at a single base position from the wild type sequence.

The term "nucleic acid molecule" refers to a polymer of DNA or RNA that can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene (Batzer et al., 1991; Ohtsuka et al., 1985; Rossolini et al., 1999).

"Operably linked" when used with respect to nucleic acid, means joined as part of the same nucleic acid molecule, suitably positioned and oriented for transcription to be initiated from the promoter. DNA operably linked to a promoter is under transcriptional initiation regulation of the promoter. Coding sequences can be operably-linked to regulatory sequences in sense or antisense orientation.

"Overexpression" refers to the level of expression in transgenic cells or organisms that exceeds levels of expression in corresponding normal or untransformed cells or organisms.

"Promoter" refers to a nucleotide sequence, usually upstream (5') to its coding sequence, which controls the expression of the coding sequence by providing the recognition for RNA polymerase and other factors required for proper transcription. An "inducible promoter" is a regulated promoter that can be turned on in a cell by an external stimulus, such as a chemical, light, hormone, stress, or a pathogen.

The terms "protein," "peptide" and "polypeptide" are used interchangeably herein.

As used herein, a "transgenic", "transformed", or "recombinant" cell refers to a genetically modified or genetically altered cell, the genome of which comprises a recombinant DNA molecule or sequence ("transgene"). For example, a "transgenic cell" can be a cell transformed with a "vector." A "transgenic", "transformed", or "recombinant" cell thus refers to a host cell such as a bacterial or yeast cell into which a heterologous nucleic acid molecule has been introduced. The nucleic acid molecule can be stably integrated into the genome by methods generally known in the art (e.g., disclosed in Sambrook and Russell, 2001). For example, "transformed," "transformant," and "transgenic" cells have been through the transformation process and contain a foreign or exogenous gene. The term "untransformed" refers to cells that have not been through the transformation process.

The term "transformation" refers to the transfer of a nucleic acid fragment into the genome of a host cell, or the transfer into a host cell of a nucleic acid fragment that is maintained extrachromosomally. A "transgene" refers to a gene that has been introduced into the genome by transformation. Transgenes may include, for example, genes that are heterologous or endogenous to the genes of a particular cell to be transformed. Additionally, transgenes may comprise native genes inserted into a non-native organism, or chimeric genes. The term "endogenous gene" refers to a native gene in its natural location in the genome of an organism. Such genes can be hyperactivated in some cases by the introduction of an exogenous strong promoter into operable association with the gene of interest. A "foreign" or an "exogenous" gene refers to a gene not normally found in the host cell but that is introduced by gene transfer.

"Vector" is defined to include, inter alia, any plasmid, cosmid, phage or other construct in double or single stranded linear or circular form that may or may not be self transmissible or mobilizable, and that can transform prokaryotic or eukaryotic host either by integration into the cellular genome or exist extrachromosomally, e.g., autonomous replicating plasmid with an origin of replication. A vector can comprise a construct such as an expression cassette having a DNA sequence capable of directing expression of a particular nucleotide sequence in an appropriate host cell, comprising a promoter operably linked to the nucleotide sequence of interest that also is operably linked to termination signals. An expression cassette also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus.

The term "wild type" refers to an untransformed cell, i.e., one where the genome has not been altered by the presence of the recombinant DNA molecule or sequence or by other means of mutagenesis. A "corresponding" untransformed cell is a typical control cell, i.e., one that has been subjected to transformation conditions, but has not been exposed to exogenous DNA.

In addition, a "wild type" gene refers to a gene, e.g., a recombinant gene, with its original or native DNA sequence, in contrast to a "mutant" gene.

II. Heavy Metal Transport System Genes, Gene Products, and Nucleic Acid Molecules of the Invention All cells are sensitive to high concentrations of heavy metals, metalloids and transition metals. Resistance to metalloid salts can be found in bacteria, fungi, parasites and animals. In these cases "resistance" is defined as cells or organisms that are relatively less sensitive than others of their same species. The most commonly utilized strategies used by all cell types for producing such resistance is the development of transport systems for the export or sequestration of heavy metals, such as arsenic (Dey and Rosen I; Rosen, 1996). In bacteria, efflux systems responsible for resistance to salts of the metalloids arsenic and antimony have been characterized (Xu et al., 1998). However, the pathways of metalloid resistance in eukaryotes are less clear. In both *Leishmania* and Chinese hamster cells, resistance correlates with active extrusion of arsenite from resistant cells (Dey et al., 1994; Wang et al., 1996), but the relevant genes or gene products have not been identified. Human multidrug resistance-associated protein (MRP), a member of the ABC transporter superfamily, also confers resistance to arsenite (Cole et al., 1994), but arsenite transport by MRP has not been demonstrated.

Three ACR (arsenic compounds resistance) genes related to resistance to arsenite and arsenate, ACR1 (GenBank Accession No. Q06596), ACR2 (GenBank Accession No. Q06597), and ACR3 (GenBank Accession No. Q06598), have been identified on chromosome XVI of the yeast *Saccharomyces cerevisiae* (Bobrowicz et al., 1997). ACR1 encodes a putative transcription factor. Insertional inactivation of ACR1 results in sensitivity to both arsenate and arsenite. ACR2 encodes a protein required for arsenate, but not arsenite, resistance that has been shown to be an arsenate reductase (Mukhopadhyay and Rosen, 1998). Acr2p is homologous to the Cdc25 superfamily of protein phosphotyrosyl phosphatases involved in cell cycle control (Fauman et al., 1998; Hofmann et al., 1998). Both types of enzymes recognize oxyanions of the pentavalent oxidation state of Group V elements, suggesting common features in their mechanisms. ACR3 encodes a plasma membrane arsenite-efflux transporter (Ghosh et al., 1999; Wysocki et al., 1997). Acr3p (404 residues, 45.8 kDa) is proposed to have ten membrane-spanning segments, and catalyzes the extrusion of arsenite from the cytosol to the extracellular medium (Wysocki et al., 1997). Acr3p is an arsenite-specific resistance protein.

Ycf1p (yeast cadmium resistance factor protein) (GenBank Accession No. NP010419), which is 63% identical to MRP1, provides a pathway for the removal of arsenite from the cytosol that is parallel to and independent of Acr3p activity (Ghosh et al., 1999). The YCF1 gene has been shown to confer resistance to Cd(II) (Szczypka et al., 1994). The YCF1 gene product, Ycf1p, pumps GS-conjugates of cadmium and other compounds into the yeast vacuole (Li et al., 1997; Li et al., 1996). Disruption of YCF1 results in sensitivity to both arsenite and arsenate to about the same level as disruption of ACR3 (Ghosh et al., 1999). Double disruption of both YCF1 and ACR3 results in hypersensitivity to arsenicals. In both cases, ACR2 is required for arsenate resistance, so reduction of arsenate to arsenite by Acr2p is a prerequisite for either Acr3p or Ycf1p function.

Cells in which ACR3 has been disrupted are unable to extrude arsenite, whereas cells in which YCF1 alone has been disrupted show normal extrusion. Vacuolar membranes exhibit accumulation of $[^{73}As](GS)_3$ in ACR3-disrupted cells, which activity is absent in YCF1-disrupted cells. Thus, each of the transporters produces arsenite resistance by removal of arsenic from the cytosol by two independent pathways. However, they differ in how and where transport occurs. Acr3p is a plasma membrane exporter that may transport the arsenite anion coupled to the membrane potential, whereas Ycf1p is a vacuolar ATP-coupled pump that leads to the accumulation of glutathione conjugates of As(III). The two proteins also differ in their specificity. Acr3p appears to be specific for metalloids, whereas Ycf1p is nonspecific, providing resistance to As(III), Sb(III) and Cd(II), and transports a variety of GS-conjugates. Clearly, the pressure of environmental exposure to As(III) has resulted in the independent evolution of distinct mechanisms to battle this ubiquitous threat.

Vacuolar membrane preparations exhibit uptake of $^{73}As$ (III) in the presence of MGATP and glutathione (GSH). No uptake was observed in vacuolar membrane vesicles prepared from a YCF1-disrupted strain. The YCF1-disrupted strain was sensitive to As(III), As(V), Sb(III), and Cd(III) whereas the ACR3-disrupted strain was sensitive to As(III) and As(V) but remained resistant to Sb(III) and Cd(II). An ACR3-YCF1 double disruption produced hypersensitivity to arsenite and arsenate. These results are consistent with ACR3 and YCF1 encoding independent transporters, either of which can confer arsenite resistance.

Any of a variety of procedures can be used to molecularly clone additional heavy metal transport system genes, i.e., genes encoding transporters, sequestration and/or resistance genes. These methods include, but are not limited to, direct functional expression of the genes following the construction of a transport system gene-containing DNA library in an appropriate expression vector system. Another method is to screen a transport system gene-containing DNA library constructed in a bacteriophage or plasmid shuttle vector with a labeled oligonucleotide probe designed from the amino acid sequence of the transport system gene or a homologous gene. It will be readily apparent to those skilled in the art that other types of libraries, as well as libraries constructed from other cells or cell types, may be useful for isolating transport system gene-encoding DNA. Other types of libraries include, but are not limited to, cDNA and genomic DNA libraries derived from other human, vertebrate, invertebrate, and lower eukaryotic cells or cell lines, other than yeast cells. For example, it will be readily apparent to those skilled in the art that suitable cDNA libraries may be prepared from cells or cell lines which have arsenic transporter activity.

Preparation of cDNA libraries can be performed by standard techniques well known in the art, such as Sambrook and Russell, 2001. It will also be readily apparent to those skilled in the art that transport system gene-encoding DNA may also be isolated from a suitable genomic DNA library. Construction of genomic DNA libraries can be performed by standard techniques well known in the art (Sambrook and Russell, 2001).

The cloned transport system gene obtained through the methods described above may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are fully described in Sambrook and Russell, supra, and are well known in the art.

III. Constructs and Host Cells of the Invention

A. DNA and Host Cells for Transformation

Vectors, plasmids, cosmids, YACs (yeast artificial chromosomes) BACs (bacterial artificial chromosomes) and DNA segments for use in transforming cells will generally comprise a heavy metal transporter encoding DNA, as well as other DNA such as cDNA, gene or genes that one desires to introduce into the cells. These DNA constructs can further include elements such as promoters, enhancers, polylinkers, or even regulatory genes as desired. One of the DNA segments or genes chosen for cellular introduction will often encode a protein that will be expressed in the resultant transformed (recombinant) cells, such as to result in a screenable or selectable trait and/or that will impart an improved phenotype to the transformed cell. However, this may not always be the case, and the present invention also encompasses transformed cells incorporating non-expressed transgenes.

DNA useful for introduction into cells includes that which has been derived or isolated from any source, that may be subsequently characterized as to structure, size and/or function, chemically altered, and later introduced into cells. An example of DNA "derived" from a source, would be a DNA sequence that is identified as a useful fragment within a given organism, and that is then chemically synthesized in essentially pure form. An example of such DNA "isolated" from a source would be a useful DNA sequence that is excised or removed from said source by biochemical means, e.g., enzymatically, such as by the use of restriction endonucleases, so that it can be further manipulated, e.g., amplified, for use in the invention, by the methodology of genetic engineering. Such DNA is commonly also referred to as "recombinant DNA."

Therefore useful DNA includes completely synthetic DNA, semi-synthetic DNA, DNA isolated from biological sources, and DNA derived from introduced RNA. The introduced DNA may be or may not be a DNA originally resident in the genotype that is the recipient of the DNA. It is within the scope of the invention to isolate a gene or regulatory region from a given genotype, and to subsequently introduce multiple copies of the gene or regulatory region into the same genotype, e.g., to enhance production of a given gene product.

The introduced DNA includes, but is not limited to, DNA from genes such as those from bacteria, yeasts, fungi, or viruses. The introduced DNA can include modified or synthetic genes, portions of genes, or chimeric genes, including genes from the same or different genotype. The term "chimeric gene" or "chimeric DNA" is defined as a gene or DNA sequence or segment comprising at least two DNA sequences or segments from species that do not combine DNA under natural conditions, or which DNA sequences or segments are positioned or linked in a manner that does not normally occur in the native genome of the untransformed cell.

The introduced DNA used for transformation herein may be circular or linear, double-stranded or single-stranded. Generally, the DNA is in the form of chimeric DNA, such as plasmid DNA, which can also contain coding regions flanked by regulatory sequences that promote the expression of the recombinant DNA present in the transformed cell. For example, the DNA may itself comprise or consist of a promoter that is active in a cell that is derived from a source other than that cell, or may utilize a promoter already present in the cell that is the transformation target.

Generally, the introduced DNA will be relatively small, i.e., less than about 30 kb to minimize any susceptibility to physical, chemical, or enzymatic degradation that is known to increase as the size of the DNA increases. The number of proteins, RNA transcripts or mixtures thereof that is introduced into the cell is preferably preselected and defined, e.g., from one to about 5-10 such products of the introduced DNA may be formed.

The selection of an appropriate expression vector will depend upon the host cells. An expression vector can contain, for example, (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the host cell or capable of integrating into the chromosome, originally containing a promoter at a site enabling transcription of the linked transporter gene.

If prokaryotes such as bacteria are used as the host, the expression vector for the transporter is preferably one capable of autonomously replicating in the micro-organism and comprising a promoter, a ribosome-binding sequence, the transporter gene, and a transcription termination sequence. The vector may also contain a gene for regulating the promoter. Suitable vectors include by way of example: for bacteria, pQE70, pQE60, pQE-9 (Qiagen), pBluescript II (Stratagene), pTRC99a, pKK223-3, pDR540, pRIT2T (Pharmacia); for eukaryotic cells: pXT1, pSG5 (Stratagene) pSVK3, pBPV, pMSG, pSVLSV40 (Pharmacia). Such commercial vectors include, for example, pKK223-3 (Pharmacia Fine Chemicals, Uppsala, Sweden) and GEM1 (Promega Biotec, Madison, Wis., USA).

If yeast is used as the host, the expression vector for the transporter is preferably one capable of autonomously replicating in the yeast. Yeast or fungal expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences. Several well-characterized yeast expression systems are known in the art and described in, e.g., Barr et al., 1989, U.S. Pat. No. 4,446,235, and European Patent Applications 103,409 and 100,561. A large variety of shuttle vectors with yeast promoters are also known to the art. However, any other plasmid or vector may be used as long as they are replicable and viable in the host.

As representative examples of appropriate hosts, there may be mentioned: bacterial cells, such as *E. coli, Streptomyces, Bacillus subtilis*; and various species within the genera *Escherichia, Pseudomonas, Serratia, Streptomyces, Corynebacterium, Brevibacterium, Bacillus, Mycobacterium*, and *Staphylococcus*, although others may also be employed as a matter of choice; fungal cells belonging to the genera *Aspergillus, Rhizopus, Trichoderma, Neurospora, Mucor, Penicillium*, etc., such as yeast belonging to the genera *Kluyveromyces, Saccharomyces, Schizosaccharomyces, Trichosporon, Schwanniomyces*, and the like.

Suitable strains of yeast for producing a transgenic yeast cell of the invention include, but are not limited to, *S. cerevisiae* W303-1A (Bowman et al., 1991) and *S. cerevisiae* MG100 (Ghosh et al., 1999). These yeast strains include a number of mutations making them desirable for use with the present invention. For example, W303-1A (MATα ade2-1 his3-11, 15 leu2-3, 112 ura3-1 trp-1) has a chromosomal ACR3 gene and is capable of extruding arsenite from the cell into the extracellular medium. The ACR3 gene of MG100 (MATα ade2-1 his3-11, 15 leu2-3, 112 ura3-1 trp-1 acr3::HIS3) is replaced with a HIS3 gene, and is not able to extrude arsenite into extracellular medium.

The construction of vectors that may be employed in conjunction with the present invention will be known to those of skill of the art in light of the present disclosure (see, e.g., Sambrook and Russell, 2001). The expression cassette of the invention may contain one or a plurality of restriction sites allowing for placement of the polynucleotide encoding a transporter under the regulation of a regulatory sequence. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter.

The expression cassette may include, in the 5'-3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences that may be a combination of synthetic and natural sequences.

The vector used in the present invention may also include appropriate sequences for amplifying expression.

B. Regulatory Sequences

A promoter is a nucleotide sequence that controls the expression of a coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. A promoter may also include a minimal promoter plus a regulatory element or elements capable of controlling the expression of a coding sequence or functional RNA. This type of promoter sequence contains of proximal and more distal elements, the latter elements are often referred to as enhancers.

Representative examples of promoters include, but are not limited to, promoters known to control expression of genes in prokaryotic or eukaryotic cells or their viruses. Particular bacterial promoters include *E. coli* lac or trp, the phage lambda $P_L$, lacI, lacZ, T3, T7, gpt, and lambda $P_R$ promoters.

Any promoter capable of expressing in yeast hosts can be used as a promoter in the present invention, for example, the GAL4 promoter may be used. Additional promoters useful for expression in a yeast cell are well described in the art. Examples thereof include promoters of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes and the like in the glycolytic pathway, heat shock protein promoter, MFa-1 promoter, CUP 1 promoter, MET, the promoter of the TRP1 gene, the ADC1 gene (coding for the alcohol dehydrogenase I) or ADR2 gene (coding for the alcohol dehydrogenase II), acid phosphatase (PHO5) gene, isocytochrome c gene, a promoter of the yeast mating pheromone genes coding for the a- or α-factor, or the GAL/CYC1 hybrid promoter (intergenic region of the GAL1-GAL10 gene/Cytochromel gene) (Guarente et al. 1982). Promoters with transcriptional control that can be turned on or off by variation of the growth conditions include, e.g., PHO5, ADR2, and GAL/CYC1 promoters. The PHO5 promoter, for example, can be repressed or derepressed at will, solely by increasing or decreasing the concentration of inorganic phosphate in the medium. Some promoters, such as the ADH1 promoter, allow high-level constitutive expression of the gene of interest.

Any promoter capable of expressing in filamentous fungi may be used. Examples are a promoter induced strongly by starch or cellulose, e.g., a promoter for glucoamylase or a-amylase from the genus *Aspergillus* or cellulase (cellobiohydrase) from the genus *Trichoderma*, a promoter for enzymes in the glycolytic pathway, such as phosphoglycerate kinase (pgk) and glycerylaldehyde 3-phosphate dehydrogenase (gpd), etc.

Two principal methods for the control of expression are known, viz.: induction, which leads to overexpression, and repression, which leads to underexpression. Overexpression can be achieved by insertion of a strong promoter in a position that is operably linked to the target gene, or by insertion of one or more than one extra copy of the selected gene. For example, extra copies of the gene of interest may be positioned on an autonomously replicating plasmid, such as pYES2.0 (Invitrogen Corp., Carlsbad, Calif.), where overexpression is controlled by the GAL4 promoter after addition of galactose to the medium. For underexpression there are two principle methods that are commonly referred to in the art as “antisense downregulation” and “sense downregulation”. Generically these processes are referred to as “gene silencing”. Both of these methods lead to an inhibition of expression of the target gene.

Several inducible promoters are known in the art. Many are described in a review by Gatz (1996) (see also Gatz, 1997). Examples include tetracycline repressor system, Lac repressor system, copper-inducible systems, salicylate-inducible systems (such as the PR1a system), glucocorticoid-inducible (Aoyama T. et al., 1997) and ecdysome-inducible systems. Also included are the benzene sulphonamide-inducible (U.S. Pat. No. 5,364,780) and alcohol-inducible (WO 97/06269 and WO 97/06268) inducible systems and glutathione S-transferase promoters.

In addition to the use of a particular promoter, other types of elements can influence expression of transgenes. In particular, introns have demonstrated the potential for enhancing transgene expression.

Other elements include those that can be regulated by endogenous or exogenous agents, e.g., by zinc finger proteins, including naturally occurring zinc finger proteins or chimeric zinc finger proteins. See, e.g., U.S. Pat. No. 5,789,538, WO 99/48909; WO 99/45132; WO 98/53060; WO 98/53057; WO 98/53058; WO 00/23464; WO 95/19431; and WO 98/54311.

An enhancer is a DNA sequence that can stimulate promoter activity and may be an innate element of the promoter or a heterologous element inserted to enhance the level or tissue specificity of a particular promoter. An enhancer is capable of operating in both orientations (5' to 3' and 3' to 5' relative to the gene of interest coding sequences), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include an enhancer element. Constructs of the invention will also include the gene of interest along with a 3' end DNA sequence that acts as a signal to terminate transcription and allow for the polyadenylation of the resultant mRNA.

As the DNA sequence between the transcription initiation site and the start of the coding sequence, i.e., the untranslated leader sequence, can influence gene expression, one may also wish to employ a particular leader sequence. Preferred leader sequences are contemplated to include those that include sequences predicted to direct optimum expression of the attached gene, i.e., to include a preferred consensus leader sequence that may increase or maintain mRNA stability and prevent inappropriate initiation of translation. The choice of such sequences will be known to those of skill in the art in light of the present disclosure.

C. Marker Genes

In order to improve the ability to identify transformants, one may desire to employ a selectable or screenable marker gene as, or in addition to, the expressible gene of interest. “Marker genes” are genes that impart a distinct phenotype to cells expressing the marker gene and thus allow such transformed cells to be distinguished from cells that do not have the marker. Such genes may encode either a selectable or screenable marker, depending on whether the marker confers a trait that one can ‘select’ for by chemical means, i.e., through the use of a selective agent (e.g., an antibiotic, or the like), or whether it is simply a trait that one can identify through observation or testing, i.e., by ‘screening’. Of course, many examples of suitable marker genes are known to the art and can be employed in the practice of the invention.

Included within the terms selectable or screenable marker genes are also genes that encode a “secretable marker” whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA and small active enzymes detectable in extracellular solution.

Selectable markers for use in prokaryotes include a tetracycline resistance or an ampicillin resistance gene. Screenable markers that may be employed include, but are not limited to, a β-glucuronidase or uidA gene (GUS) that encode an enzyme for which various chromogenic substrates are known; a beta-lactamase gene (Sutcliffe, 1978), which encodes an enzyme for which various chromogenic substrates are known (e.g., PADAC, a chromogenic cephalosporin); a xylE gene (Zukowsky et al., 1983), which encodes a catechol dioxygenase that can convert chromogenic catechols; an alpha-amylase gene (Ikuta et al., 1990); a tyrosinase gene (Katz et al., 1983) that encodes an enzyme capable of oxidizing tyrosine to DOPA and dopaquinone that in turn condenses to form the easily detectable compound melanin; a beta-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995). Selectable nutritional markers may also be used, such as HIS3, URA3, TRP-1, LYS-2 and ADE2.

IV. Gene Disruption

Several methods can be used to produce a transgenic yeast cell having a disrupted gene, e.g., by mutagenesis, e.g., insertion, deletion, substitution, homologous recombination, or by one-step gene replacement as described below. In addition, the general procedures for the generation of a transgenic yeast cell of the invention, e.g., a yeast having a disruption in the ACR3 gene and that overexpresses Ycf1p, are well known to the art and are described, for example, in Sambrook and Russell, 2001.

A. Oligonucleotide-mediated Mutagenesis

Oligonucleotide-mediated mutagenesis is one method for disrupting a gene of interest. This technique is well known in the art as described by Adelman et al. 1983. Briefly, DNA is altered by hybridizing an oligonucleotide encoding the desired mutation to a DNA template, where the template is the single-stranded form of a plasmid or bacteriophage containing the unaltered or native DNA sequence. After hybridization, a DNA polymerase is used to synthesize an entire second complementary strand of the template that will thus incorporate the oligonucleotide primer, and will code for the selected alteration in the preselected DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. 1978.

The DNA template can be generated by those vectors that are either derived from bacteriophage M13vectors (the commercially available M13 mp18 and M13 mp19vectors are suitable), or those vectors that contain a single-stranded phage origin of replication as described by Vieira et al. 1987. Thus, the DNA that is to be mutated may be inserted into one of these vectors to generate single-stranded template. Production of the single-stranded template is described, for example, in Sections 3.26-3.32 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus fommed such that one strand of DNA encodes the mutated form of the peptide, and the other strand (the original template) encodes the native, unaltered sequence of the peptide. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

B. One-step Gene Replacement Method

The one-step gene disruption procedure is based on the use of a linear fragment of DNA containing a selectable marker flanked by 5' and 3' homologous regions. The free ends of the fragment, prepared by digestion with restriction endonucleases, are recombinogenic, resulting in the integration of a gene of interest, e.g., a marker, and the loss of the targeted, wild-type allele.

Transformation must be carried out in a diploid strain if the gene encodes an essential function. Disruption of the desired genes may be verified by PCR or Southern blot analysis. The fragment required for single step disruptions can be also conveniently generated by PCR, or the gene of interest may be cloned.

Another method for producing gene disruptions, as well as simultaneously testing for the promoter activity, have been based on a dominant resistant module consisting almost entirely of heterologous DNA. Transformants resistant to a selectable marker, e.g., geneticin (G418), are selected and examined for lacZ activity. To allow for repeated use of the G418 selection, the module is flanked by short direct repeats, promoting excision in vivo.

V. Transformation

The expression cassette, or a vector construct containing the expression cassette, may be inserted into a host cell. The expression cassette or vector construct may be carried episomally or integrated into the genome of the cell, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any vector may be used as long as it is replicable and viable in the host.

A variety of techniques are available and known to those skilled in the art for introduction of constructs into a cellular host. Transformation of microbial cells may be accomplished through use of polyethylene glycol, calcium chloride, viral infection, DEAE dextran, phage infection, electroporation and other methods known in the art. Transformation of fungus may be accomplished according to Gonni et al. (1987). Introduction of the recombinant vector into yeasts can be accomplished by methods including electroporation, use of spheroplasts, lithium acetate, and the like. Any method capable of introducing DNA into cells can be used: for example, electroporation, calcium phosphate, lipofection and the like.

VI. Cultivating Yeast Cells of the Invention

Propagation of yeast cells in culture has become a regular procedure in recent years, and the yeast cells of the present invention may be grown using conventional techniques. Yeast strains of the invention may be cultured in any appropriate medium known to the art for the particular strain (see, for example, Adams et al., 1998). For example, *S. cerevisiae* strains may be grown at 30° C. in complete yeast extract/peptone/dextrose (YPD) medium supplemented with 2% glucose. Alternatively, the minimal selective medium with 2% glucose supplemented with auxotrophic requirements can be used.

As discussed above, a transgenic yeast cells of the invention may contain a selective marker, thus requiring selective conditions for culture, e.g., conditions that require the expression of a plasmid encoded gene for growth. Most selective markers currently in use are genes coding for enzymes of amino acid or purine biosynthesis. This makes it necessary to use synthetic minimal media deficient in the corresponding amino acid or purine base. However, some genes conferring antibiotic resistance may be used as well (e.g. genes conferring resistance to cycloheximide or to the amino-glycoside G 418). Yeast cells transformed with vectors containing antibiotic resistance genes may be grown in complex media containing the corresponding antibiotic whereby faster growth rates and higher cell densities can be reached. Yeast cells transformed with DNA integrating into the chromosomes do not require selective growth conditions. These transformed cells are sufficiently stable to allow growth without selective pressure. For the above reason, these cells are advantageously grown in complex media.

VII. Bioremediation and Bioreactors of the Invention

A. Methods of Bioremediation

Bioremediation techniques are destruction techniques directed toward stimulating microorganisms to grow and use target contaminants as a food and energy sources by creating a favorable environment for the microorganisms. Generally, this means providing some combination of oxygen, nutrients, and moisture, and controlling the temperature and pH. Although not all organic compounds may be amenable to biodegradation, bioremediation techniques have been successfully used to remediate water contaminated by petroleum hydrocarbons, solvents, pesticides, wood preservatives, and other organic chemicals.

The rate at which microorganisms degrade contaminants is influenced by the specific contaminants present; temperature; oxygen supply; nutrient supply; pH; the availability of the contaminant to the microorganism (clay soils can adsorb contaminants making them unavailable to the microorganisms); the concentration of the contaminants (high concentrations may be toxic to the microorganism); the presence of substances toxic to the microorganism, e.g., mercury; or inhibitors to the metabolism of the contaminant. These parameters are discussed in the following paragraphs.

To ensure that oxygen is supplied at a rate sufficient to maintain aerobic conditions, forced air, liquid oxygen, or hydrogen peroxide injection can be used. The use of hydrogen peroxide is limited because at high concentrations (above 100 ppm, 1,000 ppm with proper acclimation), it is toxic to microorganisms. Also, hydrogen peroxide tends to decompose into water and oxygen rapidly in the presence of some constituents, thus reducing its effectiveness.

Anaerobic conditions may be used to degrade highly chlorinated contaminants. This can be followed by aerobic treatment to complete biodegradation of the partially dechlorinated compounds as well as the other contaminants.

Nutrients required for cell growth are nitrogen, phosphorous, potassium, sulfur, magnesium, calcium, manganese, iron, zinc, and copper. If nutrients are not available in sufficient amounts, microbial activity will cease. Nitrogen and phosphorous are the nutrients most likely to be deficient in the contaminated environment and thus are usually added to the bioremediation system in a useable form (e.g., as ammonium for nitrogen and as phosphate for phosphorous).

Many metals that are potentially toxic to microorganisms are insoluble at elevated pH; therefore, elevating the pH of the treatment system can reduce the risk of poisoning the microorganisms.

Temperature affects microbial activity in the environment. The biodegradation rate will slow with decreasing temperature; thus, in northern climates bioremediation may be ineffective during part of the year unless it is carried out in a climate-controlled facility. Microorganisms remain viable at temperatures below freezing and will resume activity when the temperature rises. Provisions for heating the bioremediation site, such as use of warm air injection, may speed up the remediation process. Too high a temperature, however, can be detrimental to some microorganisms, essentially sterilizing the aquifer. Temperature also affects nonbiological losses of contaminants mainly through the evaporation of contaminants at high temperatures. The solubility of contaminants typically increases with increasing temperature; however, some hydrocarbons are more soluble at low temperatures than at high temperatures. Additionally, oxygen solubility decreases with increasing temperature.

Treatability or feasibility studies may be performed to determine whether bioremediation would be effective in a given situation. The extent of such a study can vary depending on the nature of the contaminants and the characteristics of the site.

Bioreactors degrade contaminants in water with microorganisms through attached or suspended biological systems. In suspended growth systems, such as activated sludge, fluidized beds, or sequencing batch reactors, contaminated water is circulated in an aeration basin where a microbial population aerobically degrades organic matter and produces $CO_2$, $H_2O$, and new cells. The cells form a sludge, which is settled out in a clarifier, and is either recycled to the aeration basin or disposed. In attached growth systems, such as upflow fixed film bioreactors, rotating biological contactors (RBCs), and trickling filters, microorganisms are established on an inert support matrix to aerobically degrade water contaminants.

B. Bioreactors

Bioreactors provide an alternative to the use of physical methods, e.g., carbon adsorption onto activated charcoal units, air stripping and membrane separation, and chemical methods, e.g., precipitation and oxidation/reduction, for the remediation of contaminated water. Any one of a number of bioreactors known to the art can be used with the transgenic yeast cell of the invention for the bioremediation of contaminated water. For example, wastewater treatment bioreactors known to the art are disclosed in, for example, U.S. Pat. No. 3,821,087, U.S. Pat. No. 4,266,026, U.S. Pat. No. 4,279,753, U.S. Pat. No. 4,804,628, U.S. Pat. No. 5,578,214, U.S. Pat. No. 5,582,732, U.S. Pat. No. 5,656,421, U.S. Pat. No. 5,702,604, U.S. Pat. No. 5,702,604 and U.S. Pat. No. 5,753,110.

Bioreactors of the invention can employ either aerobic or anaerobic processes for remediation. Aerobic processes have been more commonly employed due to their effectiveness in converting contaminants into less harmful substances. More specifically, biofilms have been widely used because an active biomass produced in the reactor allows large volumetric loadings and good effluent quality without the need for solids separation. The biofilm bioreactors have been generally categorized as continuously stirred tank reactors (CSTRs), fixed-bed and fluidized bed.

In the CSTR, the liquid (i.e., waste water) is completely mixed, such as by mechanical stirring, while an activated biomass grows and uniformly contacts the liquid without attachment to a media. In the fixed-bed reactor, the biofilm attaches to an immobile solid media while the liquid passes through the reactor. In the fluidized bed reactor, the liquid flows through the reactor at a sufficiently high rate to fluidize the solid media. Thereby, the solid media and attached biofilm are mixed throughout the reactor. In both the fixed-bed and fluidized-bed bioreactors, the effluent can be recycled. A primary effect of recycling is to dilute the feed. Furthermore, evenly distributing the feed or nutrient throughout the bioreactor promotes more uniform growth of the biofilm throughout the reactor. In fixed-bed bioreactors, the bioreactors can be classified as hollow fiber membrane or packed bed. In the former, a tubular or a hollow fiber membrane is used as the carrier or medium on which the biofilm can grow. In the latter, ceramic porous bodies in multi-layered plates, or hydrophobic polyurethane foams and pall rings (as in U.S. Pat. No. 5,217,616), have been used as the medium. In the hollow fiber membrane bioreactor, oxygen or air is transported through the lumens of the hollow fibers by a pressure gradient applied to the membrane interfaces. The biofilm is typically grown in the fluid space between the outer shells of the hollow fiber membrane and the shell wall of the bioreactor.

The oxygen required for biofilm growth can be supplied by several commonly used methods such as aeration through bubble diffusers and permeation through membranes. Oxygen permeates or transports through a non-porous polymer membrane when a pressure gradient is applied between the two interfaces of the membrane. The permeation process occurs by a solution-diffusion mechanism that is commonly controlled by the molecular diffusion of oxygen in the polymer matrix of the membrane. At the same time, solution equilibrium is established between the oxygen molecules in a gas phase in contact with the membrane interfaces and the molecules dissolved in the polymer at those interfaces. If one of the membrane interfaces is in contact with a liquid phase, then oxygen transfer from the gas phase to the liquid phase through the membrane also occurs by the solution-diffusion mechanism. A bubbleless oxygen transfer to the liquid phase can then be achieved by controlling the gas phase oxygen pressure. In a micro-gravity environment, oxygenation of the liquid phase through a conventional bubble diffuser method is no longer possible due to the difficulties associated with phase separation. Utilization of a membrane to oxygenate a liquid in a micro-gravity environment eliminates the two-phase fluid flow problem.

Contaminants in water are put into contact with microorganisms in attached or suspended growth biological reactors. In suspended systems, such as activated sludge, contaminated water is circulated in an aeration basin. In attached systems, such as rotating biological contractors and trickling filters, microorganisms are established on an inert support matrix.

The invention will now be illustrated by the following non-limiting Examples.

EXAMPLE 1

Construction of a Transgenic *Saccharomyces cerevisiae* Strain for Arsenic Bioremediation Introduction The first step in arsenate detoxification is biotransformation of As(V) to As(III) by Acr2p, an enzyme that catalyzes arsenate reduction (Mukhopadhyay and Rosen, 1998). The fact that *S. cerevisiae* yeast cells reduce arsenate to arsenite in vivo means that the process described herein bioremediates both As(V) and As(III).

The ACR2 gene has been cloned and expressed (Bobrowicz et al., 1997; Mukhopadhyay and Rosen, 1998), and its product, an arsenate reductase enzyme, has been expressed and purified. Reduction is usually not limiting for arsenic detoxification. However, if some water supplies are particularly high in As(V) such that reduction becomes rate limiting for removal of arsenic from the water, the ACR2 gene in yeast can be overexpressed.

Arsenite is detoxified by one of two pathways (Ghosh and Rosen, 1999). In one pathway, arsenite is extruded out of the cells by a plasma arsenite membrane carrier, Acr3p (Wysocki et al., 1997; Ghosh and Rosen, 1999). In the other pathway cytosolic As(III) is conjugated with glutathione, and the conjugate is sequestered in the vacuole by Ycf1p, a pump for metal-glutathione conjugates (Ghosh and Rosen, 1999; Li et al., 1997; Li et al., 1996). The construction of a strain in which Acr3p is inactivated by disruption of the ACR3 gene, and the YCF1 gene for the vacuolar $As(GS)_3$ pump is overexpressed, is described herein. This strain can no longer expel arsenic back into the environment but instead hyperaccumulates arsenite. While reports of the individual genes and their functions in arsenic transport have been published (Bobrowicz et al., 1997; Ghosh et al., 1999; Li et al., 1996; Li et al., 1997; Wysocki et al., 1997), the present genetically engineered yeast strain has the combination of deletion of ACR3 from the yeast chromosome in conjunction with YCF1 on a plasmid.

Materials and Methods

Strains and plasmids: *S. cerevisiae* strains W303pYCF1 and MG100pYCF1 were developed specifically for this study.

To produce strain W303pYCF1, *S. cerevisiae* W303 (see Table 1), which contains a chromosomal ACR3 gene and can extrude arsenite into the extracellular aqueous solution, was transformed with plasmid pYCF1 (Table 1), which contains a 4.5 Kb fragment of the YCF1 gene. To prepare MG100 pYCF1, first *S. cerevisiae* MG100 (Table 1) was derived from strain W303 by gene replacement of the yeast's ACR3 gene with a HIS3 gene. Strain MG100 can not extrude arsenite into the extracellular aqueous solution. Then, strain MG100 was transformed with plasmid pYCF1 (Table 1) to develop a strain capable of arsenic hyperaccumulation.

TABLE 1

Strains and plasmids

| Strains | Genotype/description | Source |
|---|---|---|
| *S. cerevisiae* Strains | | |
| W303-1A | MATα ade2-1 his3-11, 15 leu2-3, 112 ura3-1 trp-1 | Bowman et al. 1991 |
| MG100 | MATα ade2-1 his3-11, 15 leu2-3, 112 ura3-1 trp-1 acr3::HIS3 | Ghosh et al., 1999 |
| Plasmids | | |
| pGEM-T | *E. coli* cloning vector, $Ap^r$ | Promega |
| pGEM-T-YCF1 | 4.5 kbp PCR fragment containing YCF1 cloned in pGEM-T | Herein |
| pYES2.0 | Multicopy, shuttle vector, $Ap^r$, URA3, gal1 | Invitrogen |
| pYCF1 | 4.5 kbp BamHI-NotI fragment containing YCF1 cloned into BamHI-NotI digested pYES2.0 | Herein |

Media

*S. cerevisiae* strains were grown at 30° C. in complete YPD medium supplemented with 2% glucose (Adams et al., 1998). Alternatively, the minimal SD medium with 2% glucose supplemented with auxotrophic requirements was used (Adams et al., 1998). *E. coli* cells were grown in LB medium supplemented when necessary with 125 μg/ml ampicillin (Sambrook and Russell, 2001).

DNA Manipulations: Cloning procedures (plasmid purification, restriction digestion, endonuclease and exonuclease digestion, gel electrophoresis, polymerase chain reaction (PCR), ligation, dephosphorylation and *E. coli* transformation) were carried out as described (Guthrie and Fink, 1991; Sambrook and Russell, 2001). Transformation of yeast cells was carried out using a lithium acetate method (Ito et al., 1983). Yeast genomic DNA was isolated using QIAamp spin colum according to the manufacturer's directions (Qiagen Inc.).

Disruption of the ACR3 gene: Disruption of the ACR3 gene was carried out by a one-step gene replacement method (Ghosh et al., 1999). A 3.1-kilobase (kb) fragment of yeast genomic DNA containing ACR3, ACR2, and a portion of ACR1 was amplified by PCR using a forward primer 5'-CGACATAAGCTTATCTTGTCC-3' (SEQ ID NO:1) that hybridizes with a region 533 bp downstream of ACR3 and a reverse primer 5'-GTCATTTGAGAGATTCGTACAGC-3' (SEQ ID NO:2) that hybridizes to a region 483 bp inside of ACR1. The fragment was ligated into pGEM-T. The resulting plasmid pGEM-T-ACR3, carrying ACR3, ACR2, and a portion of ACR1, was digested with KpnI. The linearized plasmid was made blunt with T4 DNA polymerase, was digested with BamHI, which excised a 1,145-bp fragment that included all but the first 34 bp and last 35 bp of ACR3, and was ligated with a 1.7-kb HIS3 gene that had been obtained from plasmid pUC18-HIS3-1 as a 1,769-bp BamHI-SmaI fragment. The resulting plasmid was digested with EcoRI, and the 3.6-kbp fragment was isolated, purified, and transformed into yeast strain W303-1B, producing the ACR3Δ strain MG100 by homologous recombination. Recombinants were selected for growth in the absence of histidine and were screened for arsenite sensitivity. Replacement of the ACR3 gene by the HIS3 gene was verified by PCR using a forward primer 5'-AGATCTATGTCAGAAGATCAAAAAAGTG-3' (SEQ ID NO:3) that introduces a Bgl II site immediately in front of the first ACR3 codon and hybridizes from that point. The reverse primer was 5'-GAATTCATTTCTATTGTTCCATATATAATATGGTTTAAGGATCCTCG-3' (SEQ ID NO:4), which hybridizes at the last ACR3 codon and introduces an EcoRI site immediately following ACR3.

Construction of yeast plasmids and transformation: A 4.5 Kb YCF1 gene (with BamH1 at the 5'-end and Not1 at the 3'-end) was cloned into plasmid pGEM-T by PCR using genomic DNA from *S. cerevisiae* W303 as template. The BamH1/NotI digested 4.5 kb YCF1 gene was then cloned in yeast expression vector pYES2.0 (Table 1) under the control of the GAL4 promoter. This plasmid, called pYCF1, was transformed into *S. cerevisiae* W303, creating strain W303 pYCF1, and transformed into *S. cerevisiae* MG100, creating strain MG100 pYCF1. In these strains galactose was added to induce YCF1 expression, and glucose was added to repress its expression.

Metal ion resistance assays: Strains were grown over night at 30° C. in liquid minimal selective medium (SD medium) with either 2% glucose or 2% galactose and appropriate supplements. The cultures were diluted into minimal media to an absorbance at 600 nm of 0.1 in the presence of varying concentrations of the indicated metal ions. The cultures were then incubated for an additional 24 hours, after which growth was estimated from the absorbance at 600 nm. For growth on solid media, cells were streaked from single colonies and were incubated for 3-4 days at 30° C.

Transport assays: For uptake assays in vivo, a single colony of each strain was inoculated and grown in yeast extract/peptone/dextrose medium containing 2% glucose at 30° C. to exponential phase ($OD_{600}$=1.0), followed by induction with 2% galactose. The cells were washed twice with cold degassed transport water and once with degassed transport buffer (75 mM Hepes, 150 mM KCl, 1 mM $MgCl_2$, pH 7.2) and were suspended at a density of $1\times10^8$ cells/ml in degassed transport buffer. To initiate the assay, 0.1 ml of cells was diluted with 0.9 ml of the same buffer containing 0.1 M glucose. After 30 minutes at 30° C., $Na_2{}^{73}AsO_2$ was added to a final concentration of 1.0 μM. Portions (0.1 ml) were withdrawn at intervals and were filtered through nitrocellulose filters (0.2 μm pore size; Whatman). The filters were washed with 5 ml of the above buffer at room temperature and were dried. Radioactivity was quantified in liquid scintillation counter. $Na_2{}^{73}AsO_2$ was prepared by reduction of radioactive arsenate.

Results

The wild type strain, W303, is resistant to higher concentrations of sodium arsenite because it extrudes the arsenite out of the cells by the Acr3p arsenite carrier protein (FIG. 1). Expression of Ycf1p on a plasmid has no effect on resistance in this strain. The ACR3-deleted strain MG100 is unable to extrude arsenite and thus is extremely arsenic sensitive. Expression of Ycf1p on a plasmid in MG100 restores arsenite resistance because the $As(GS)_3$ conjugate is sequestered in the vacuole.

Figure 2:
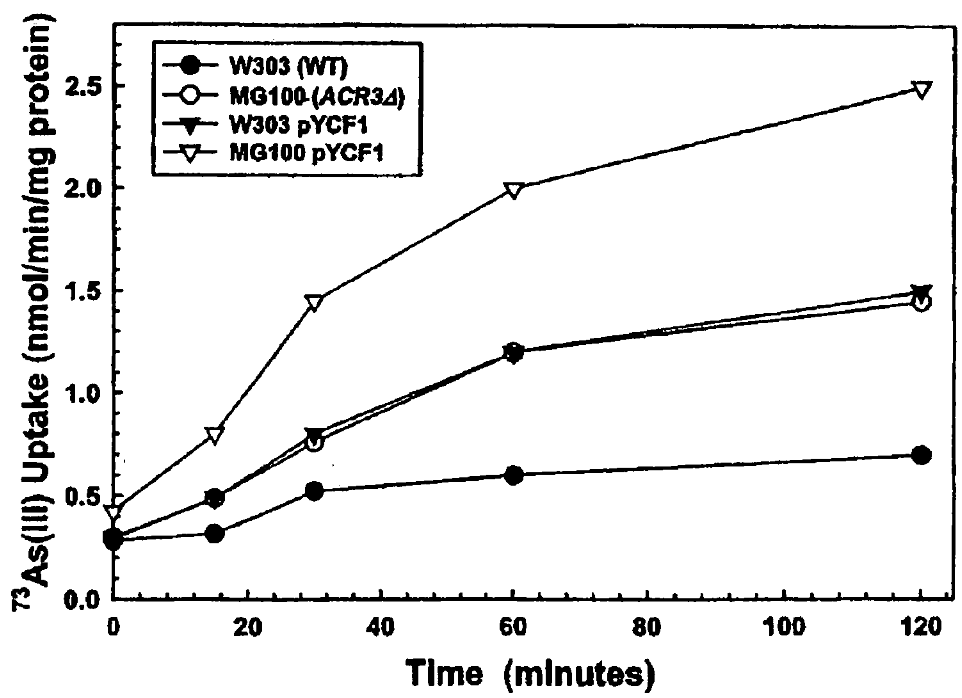
FIG. 2. Arsenite transport from cells of *S. cerevisiae*. Accumulation of $^{73}As(OH)_3$ was measured in intact cells. Strains were closed circles: W303 (wild type ACR3); closed inverted triangles: W303 pYCF1; open circles: MG100 (ACR3Δ); open inverted triangles: MG100 pYCF1.

In FIG. 2, the wild type strain, W303, is shown to accumulate the least arsenic because it extrudes the arsenite out of the cells by the Acr3p arsenite carrier protein. Expression of Ycf1p on a plasmid increases the amount of radioactive arsenite accumulated because it sequesters $As(GS)_3$ in the vacuole. The ACR3-deleted strain MG100 accumulates more $^{73}As(III)$ than the wild type because it is unable to extrude arsenite. When the YCF1 gene is expressed in MG100 from plasmid pYCF1, the cells accumulate much higher amounts of arsenite, which can occur only if the aqueous medium is becoming depleted of arsenite.

EXAMPLE 2

Arsenite Transport by Mammalian Aquaglyceroporins AOP7 and AQP9

Introduction

The U.S. Environmental Protection Agency has classified arsenic as a human carcinogen (Smith et al., 1992). Conversely, trivalent arsenic is an effective chemotherapeutic agent for the treatment of acute promyelocytic leukemia (Soignet et al., 1998). For a complete understanding of the mechanisms of arsenic toxicity and carcinogenesis as well as its ability to serve as a chemotherapeutic agent, it is necessary to identify the routes of arsenite uptake and efflux from cells (Rosen I; Ghosh and Rosen, 2002). Arsenic is bioavailable in either of two oxidation states, As(V) (arsenate) or As(III) (arsenite). Pentavalent arsenic is transported into cells via phosphate transport systems in both prokaryotes (Willsky and Malamy, 1980) and eukaryotes (Bun-ya et al., 1996). It is reduced to the more toxic trivalent arsenite by arsenate reductases (Ji et al., 1994; Gladyshera et al., 1994; Mukhopadhyay et al., 2000). Arsenite can be detoxified either by extrusion from cells or by sequestration within intracellular organelles as thiol conjugates (Rosen I; Ghosh and Rosen, 2002; Tamas & Wysocki, 2001). In *Saccharomyces cerevisiae*, Acr3p is an arsenite extrusion system (Wysocki et al., 1997; Ghosh et al., 1999), and the ABC transporter Ycf1p catalyzes uptake of $As(GS)_3$ into the vacuole (Ghosh et al., 1999).

The routes of uptake of arsenite are less well defined. In *Escherichia coli*, disruption of the glpF gene led to increased tolerance for antimonite, which is chemically similar to arsenite (Sanders et al., 1997). GlpF facilitates glycerol uptake (Heller et al., 1980; Sweet et al., 1990) and is a bacterial member of the aquaporins, a family of membrane proteins that includes water-selective pores (aquaporins) and multifunctional channels (aquaglyceroporins), which also transport organic polyols and urea (Borgnia et al., 1990). It is likely that GlpF recognizes the un-ionized form of antimonite, $Sb(OH)_3$, transporting it as the inorganic equivalent of a polyol. With a pKa of 11.8, this protonated form would predominate in neutral solutions. Although the glpF mutant did not exhibit increased arsenite tolerance, GlpF also transports $As(OH)_3$, the primary ionization state of arsenite in neutral solutions. Redundancy in arsenic transporters dampens the effect of the glpF mutation (Sanders et al., 1997). Recently the GlpF homolog Fps1p, a *S. cerevisiae* aquaglyceroporin (Van Aelst et al., 1991), was clearly shown to be involved in uptake of arsenite (Wysocki et al., 2001). Deletion of the FPS1 gene resulted in increased tolerance to both arsenite and antimonite, and fps1Δ cells exhibited decreased uptake of radioactive arsenite. Although *E. coli* GlpF has a physiological role for uptake of glycerol, yeast Fps1p functions primarily as a glycerol efflux pathway for osmoregulation (Luyten et al., 1995).

The mammalian aquaglyceroporin subfamily includes AQP3, AQP7, and AQP9, of which AQP9 has broadest solute permeability (Borgnia et al., 1999). In this report the *Rattus norvegicus* AQP9 (Tsukaguchi et al., 1998) cDNA was cloned into an *S. cerevisiae* expression vector under control of the GAL4 promoter, and its ability to substitute for Fps1p in metalloid uptake was examined. A strain of *S. cerevisiae* was constructed from which the genes encoding FPS1 and the two arsenite efflux transporters, Acr3p and Ycf1p, were deleted. Compared with a wild-type strain, an acr3Δ ycf1Δ strain is hypersensitive to both arsenite and antimonite (Ghosh et al., 1999). Deletion of FPS1 in the acr3Δ ycf1Δ strain increased tolerance to both metalloids, in agreement with the results of Wysocki et al. (Wysocki et al., 2001). Galactose-inducible expression of membrane-bound AQP9 was observed, and AQP9 expression made the triple deletion strain more sensitive to arsenite and antimonite in a galactose-dependent fashion. Cells of the acr3Δ ycf1Δ strain accumulate more $^{73}As(OH)_3$ than a wild-type strain because they are unable to extrude arsenite (Ghosh et al., 1999). Cells of the fps1Δ acr3Δ ycf1Δ strain accumulated less arsenite than the acr3Δ ycf1Δ strain, consistent with Fps1p facilitating arsenite uptake (Wysocki et al., 2001). AQP9 expression resulted in increased transport of both $^{73}As(OH)_3$ and $^{125}Sb(OH)_3$, demonstrating that AQP9 can functionally substitute for Fps1p in the transport of metalloids. In contrast, when the *Mus musculus* AQP7 cDNA was cloned into the same yeast vector, no AQP7 was expressed. However, *Xenopus oocytes* microinjected with either AQP7 or AQP9 cRNA exhibited a 10-fold increase in $^{73}As(OH)_3$ permeability, indicating that both aquaglyceroporins recognize and transport arsenite.

Strains and Plasmids. Plasmids and *S. cerevisiae* strains used in this study are described in Table 2. *E. coli* strain JM109 [recA1 supE44 endA1 hsdR17 gyrA96 relA1 thi Δ (lac-proAB) F (traD36 proAB$^+$ lacI$^q$ lacZΔM15] and JM110 [rps (Str$^r$) thr leu thi-1 lacY galK galT ara tonA tsx dam dcm supE44 Δ(lac-proAB) [F traD36 proAB lacIqZΔM15] were used for molecular cloning.

TABLE 2

Strains and plasmids

| Strains/ plasmids | Genotype/description | Source |
|---|---|---|
| *S. cerevisiae* Strains | | |
| W303-1B | MATα ade2-1 his3-11, 15 leu2-3, 112 ura3-1 trp-1 | Bowman et al., 1991 |
| DTY167 | MATα ura3-52 his6 leu2-3, 112 his3-Δ, 200 trp1-901 lys2-80 suc $\overline{2}$ Δycf1::hisG | Li et al, 1996 |
| MG102 | MATα ura3-52 his6 leu2-3, 112 his3-Δ, 200 trp1-901 lys2-801 suc $\overline{2}$ Δycf1::hisG acr3::URA3 | Ghosh et al., 1999 |
| HD9 | MATα ura3-52 his6 leu2-3, 112 his3-Δ, 200 trp1-901 lys2-801 suc $\overline{2}$ Δycf1::hisG acr3::URA3 fps1::leu | Herein |
| Plasmids | | |
| pGEM-T | *E. coli* cloning vector, Ap$^r$ | Promega |
| pYES3 | *S. cerevisiae-E. coli* shuttle vector, Ap$^r$, TRP3 | Invitrogen |
| pGEM-T-FPS1 | 1,941-kbp PCR fragment containing FPS1 cloned in pGEM-T | Herein |
| pUC18 | *E. coli* cloning vector, Ap$^r$ | Yanisch-Perron et al., 1985 |
| pUC18-LEU2 | 3.0-kbp BglII fragment containing LEU2 ligated into BglII site of pUC18 | Herein |
| pX-βG-ev1 | Cloning vector | Preston et al., 1992 |
| pX-βG-ev1-AQP9 | *Rattus norvegicus* AQP9 gene cloned into the BglII site of pXβG-ev1 | Herein |
| pAQP9 | 1.1-kbp HindIII-KpnI fragment containing AQP9 cloned into HindIII-KpnI-digested pYES3 | Herein |
| pX-βG-ev1-APQ7 | *Mus musculus* AQP7 gene cloned into the BglII site of pXβG-ev1 | Herein |
| pAQP7 | 1.2-kpb EcoRI fragment containing AQP7 cloned into EcoRI-digested pYES3 | Herein |

Media. *S. cerevisiae* strains were grown at 30° C. in complete yeast extract-peptone-dextrose (2%) or yeast extract-peptone-glycerol (2%) medium (Adams et al., 1998). Alternatively, the minimal SD medium (Adams et al., 1998) supplemented with either 2% galactose or 2% glucose and with auxotrophic requirements. *E. coli* cells were grown in LB medium (Sambrook and Russell, 2001) supplemented when necessary with 125 μg/ml ampicillin.

DNA Manipulations. Plasmid purification, restriction digestion, endonuclease and exonuclease digestions, gel electrophoresis, PCR, ligation, dephosphorylation, and *E. coli* transformations were carried out as described (Sambrook et al., 1989; Guthrie and Fink, 1991). Transformation of yeast cells was carried out by using a Geno easy-transform kit (Geno Technologies, St. Louis, Mo.). Yeast genomic DNA was isolated by using QIAamp spin column according to the manufacturer's directions (Qiagen).

Deletion of the FPS1 Gene. The FPS1 gene was deleted by a one-step gene replacement method (Rothstein, 1983). A 1,941-bp fragment of yeast genomic DNA containing FPS1 was PCR amplified with a forward primer 5'-ATGAGTAATCCTCAAAAAGC-3' (SEQ ID NO:5) that hybridizes with the start of the FPS1 gene and a reverse primer 5'-TCATGTTACCTTCTTAGC-3' (SEQ ID NO:6) that hybridizes to the end of the coding sequence. The fragment was ligated into vector pGEM-T and transformed into *E. coli* JM110. The resulting plasmid, pGEM-T-FPS1, was isolated and digested with StuI, which produced a 1,245-bp fragment that was 427 bp from the start and 269 bp from the end of the FPS1 gene. The 3-kbp LEU2 gene was isolated from plasmid pUC18-LEU2 by digestion with PstI and AlwNI to cut out the LEU2 gene and with SmaI to digest the remaining vector DNA. The FPS1 and LEU2 fragments were ligated together, and the resulting plasmid was digested with PstI and SphI. The 3.7-kbp fragment was isolated, purified, and transformed into yeast strain MG102 (acr3Δycf1Δ), producing the fps1Δ acr3Δ ycf1Δ strain HD9 by homologous recombination. Recombinants were selected for growth in the absence of leucine and were screened for arsenite sensitivity. Deletion of FPS1 was verified by PCR by using the forward and reverse primers described above.

Cloning AOP7 and AOP9 into the *S. cerevisiae* Expression Vector pYES3. AQP7 cDNA was amplified by reverse transcription-PCR of mouse adipocyte total RNA by using forward primer 5'-GGGGAATTCAGATCTATGGCCCCCAGGTCTGTGCTG-3' (SEQ ID NO:7) and reverse primer 5'-GGGGAATTCAGATCTTTAGAAGTGCTCTAGAGGCAC-3' (SEQ ID NO:8). AQP9 cDNA was amplified by reverse transcription-PCR from rat liver total RNA from Ambion by using a forward 5'-GGGAGATCTGAATTCATGCCTTCTGAGAAGGACGGTGC-3' (SEQ ID NO:9) and reverse primer 5'-GGGAGATCTGAATTCCTACATGATGACACTGAGCTCG-3' (SEQ ID NO:10). PCR products were digested with BglII and cloned into BglII-digested vector pXβG-ev1, producing plasmids pXβG-ev1-AQP7 and pXβG-ev1-AQP9. The AQP7 and AQP9 genes were sequenced, and an A93V polymorphism was found in AQP9, which was corrected to the published Ala-93 by site-directed mutagenesis. Plasmid pXβG-ev1-AQP9 was digested with HindIII and KpnI. A 1.1-kbp fragment containing the AQP9 gene was ligated into HindIII-KpnI digested plasmid pYES3. The ligation mixture was transformed into *E. coli* strain JM109, and the resulting plasmid, pAQP9, was isolated and transformed into yeast strain HD9. The transformants were selected on minimal SD medium without tryptophan. Plasmid pAQP7 was prepared similarly. Plasmid pXβG-ev1-AQP7 was digested with HindIII and SpeI. The linearized 1.2-kbp fragment containing AQP7 was made blunt by using large fragment of DNA polymerase I. Vector plasmid was digested with EcoRI, and the ends were made blunt by using large fragment of DNA polymerase I. The two blunt-end DNAs were ligated together, and the ligation mixture was transformed into *E. coli* strain JM109. A plasmid with the correct insert, termed pAQP7, was isolated and transformed into yeast strain HD9. The transformants were selected on minimal SD medium without tryptophan. The constructs for pAQP7 and pAQP9 were sequenced to confirm that they retained the reported DNA sequences.

Metal Ion Resistance Assays. Strains were grown overnight at 30° C. in liquid SD medium with either 2% glucose or 2% galactose and the appropriate supplements. The cultures were diluted into minimal media to an $OD_{600}$ of 0.1 in presence of varying concentrations of the indicated metalloid salts, incubated for an additional 20 hours, following which the growth was estimated from $OD_{600}$. For growth on solid media, cells were streaked from single colonies and incubated for 3-4 days at 30° C.

Transport Assays. In vivo metalloid uptake assays were performed as described (Ghosh et al., 1999). In brief, cells were grown to exponential phase at 30° C. in either YPG medium or SD medium with 2% galactose in place of glycerol. The cells were harvested, washed twice with degassed transport buffer consisting of 75 mM Hepes, 150 mM KCl, and 1 mM $MgCl_2$ (pH 7.3), and suspended to a density of $2\times10^9$ cells/ml in the same buffer, all at 4° C. To initiate the assay, 0.1 ml of cells was diluted with 0.9 ml of transport buffer containing 0.1 M glucose. After 30 minutes at 30° C., $Na_2{}^{73}AsO_2$ or $K(^{125}Sb)$tartrate was added to a final concentration of 5 μM. When used as an inhibitor, glycerol was added to a final concentration of 200 mM 20 min before the radioactive metalloid. Portions (0.1 ml) were withdrawn at intervals and filtered through nitrocellulose filters (0.2-μm pore size; Whatman). The filters were washed with 5 ml of room temperature transport buffer and dried, and the radioactivity was quantified in liquid scintillation counter. $Na_2{}^{73}AsO_2$ and $K(^{125}Sb)$tartrate were prepared by reduction of radioactive arsenate or antimonate (Reay and Asher, 1977). $^{73}As$ was obtained from Los Alamos National Laboratories. $^{125}Sb$ was purchased from New England Nuclear.

Transport in *Xenopus laevis oocytes* was performed as described (Preston et al., 1992). Plasmids pXβG-ev1-AQP7 and pXβG-ev1-AQP9 were linearized with NotI and XbaI, respectively. Capped cRNAs were synthesized in in vitro reactions by using the linearized plasmids. Oocytes from *Xenopus laevis* were defolliculated and injected with 5 ng of AQP7 cRNA, 25 ng of AQP9 cRNA, or 50 nl of water. They were then incubated at 18° C. for 3 days in Barth's solution (Preston et al., 1992). For transport assays the *oocytes* were incubated with 0.5 ml of Barth's solution containing 3 μM $^{73}As(OH)_3$. After 90 seconds the assay solution was removed, and the *oocytes* were washed with same solution without labeled arsenite. The *oocytes* were then solubilized with 0.2 ml of 10% SDS, and radioactivity was quantified in liquid scintillation counter.

Immunological Detection of AQP7 and AQP9 Expression. Membranes for immunoblot analysis of AQP7 and AQP9 expression were prepared as described previously (Ghosh et al. 1999). The membranes were analyzed for AQP7 and AQP9 expression by PAGE and immunoblotting. Samples containing 25 μg, 100 μg and 200 μg of prepared membranes were dissolved in 0.1 ml of SDS sample buffer, incubated for 2 hours at room temperature and analyzed by SDS/PAGE (Laemmli, 1970) by using a 12% polyacrylamide gel. Proteins were electrophoretically transferred to a nitrocellulose membrane (0.2-μm pore size) and immunoblotted overnight at 12 mV and 4° C. with an antibody directed against either AQP7 or AQP9 (Alpha Diagnostic, San Antonio) at a dilution of 1:5,000 or 1:4,000, respectively. A chemiluminescent assay was used to detect the antigen-Ab reaction. The filter was incubated with 10 ml of the enhanced chemiluminescence solution (New England Nuclear) and exposed on x-ray film for 10 seconds at room temperature.

AQP9 Complements the Metalloid Resistance Phenotype of an fps1Δ Strain of *S. cerevisiae*. Two microbial aquaglyceroporins have been shown to facilitate metalloid uptake, GlpF in *E. coli* (Sanders et al, 1999) and Fps1p in *S. cerevisiae* (Wysocki et al., 2001). The most closely related mammalian homologs to the two microbial proteins are AQP7 and AQP9. *R. norvegicus* AQP9 is 32% identical and 52% similar to Fps1p. *M musculus* AQP7 is slightly more distant, with 28% identity and 44% similarity to Fps1p. Both mammalian proteins are more distant from the prokaryotic aquaglyceroporin, but AQP7 and AQP9 are more closely related to each other, sharing 52% identity and 68% similarity.

The ability of AQP7 and AQP9 to substitute for Fps1p in yeast was examined. Strain MG102 (acr3Δ ycf1Δ) is hypersensitive to metalloids because the genes for Acr3p and Ycf1p have been deleted (Ghosh et al., 1999). MG102 was used to construct a triple fps1Δ acr3Δ ycf1Δ strain, HD9. The two mammalian cDNAs were cloned into the yeast expression vector pYES3 under control of the GAL4 promoter, and galactose-dependent expression was examined.

Membranes were prepared from cells of strain HD9 and HD9 pAQP9, each grown in the absence and presence of 2% galactose. When pAQP9 was introduced into strain HD9, cell membranes contained bands at approximately 25 and 50 kDa when induced with galactose (data not shown). As is often observed (Borgnia et al., 1999), the immunologically reacting bands migrated slightly faster than expected for the mass of a monomer and dimer of the 32-kDa AQP9. In contrast, no immunologically reacting material was found in membranes from cells transformed with pAQP7 (data not shown).

Figure 3A:
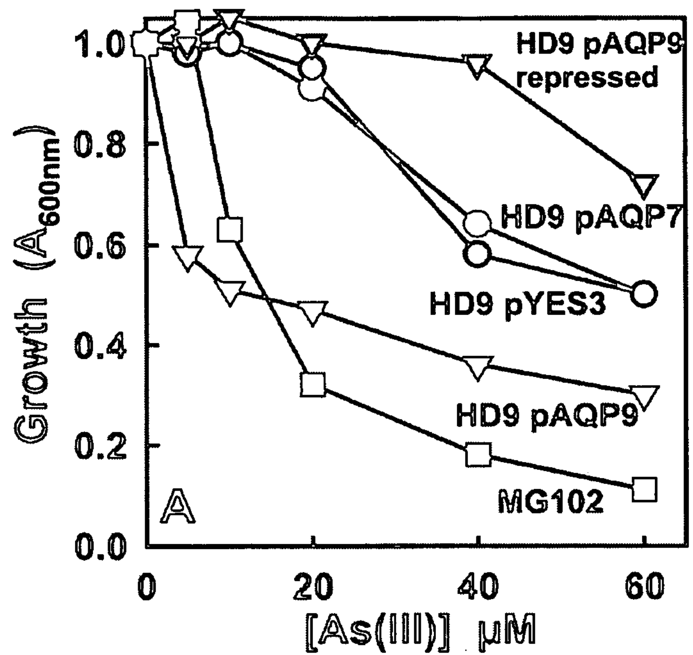
FIG. 3. AQP9 functionally complements the metalloid sensitivity of *S. cerevisiae* fps1Δ. Growth was measured in liquid SD minimal medium with 2% galactose (or, if repressed, glucose) in the presence of the indicated concentrations of sodium arsenite (A), potassium antimonyl tartrate (B), sodium arsenate (C), or cadmium chloride (D). Strains were: □, MG102 (acr3Δ ycf1Δ); ○, HD9 (fps1Δ acr3Δ ycf1Δ) pYES3; ●, HD9 pAQP7 (induced); ▼, HD9 pAQP9 (induced); and ∇, HD9 pAQP9 (repressed).
Figure 3B:
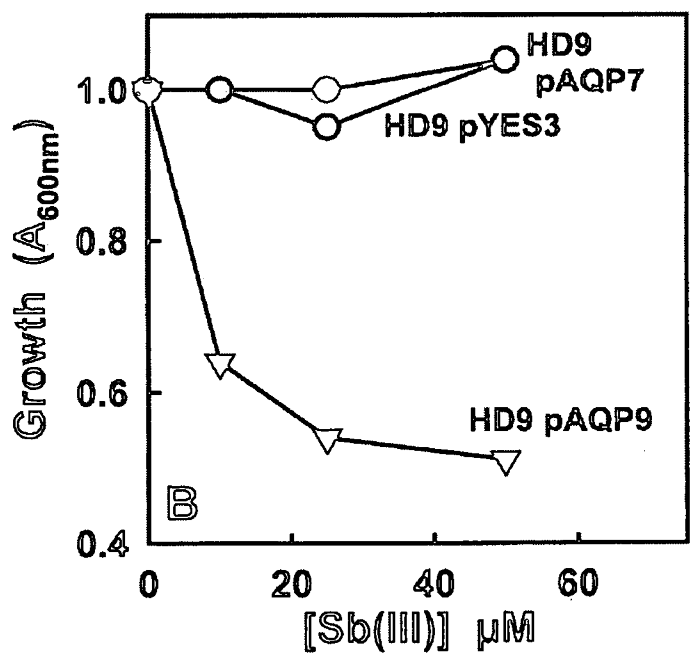
Figure 3C:
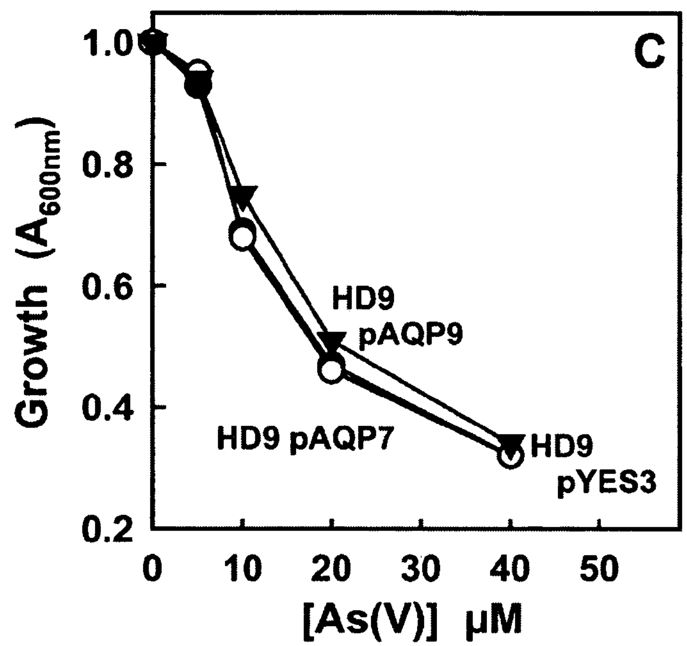
Figure 3D:
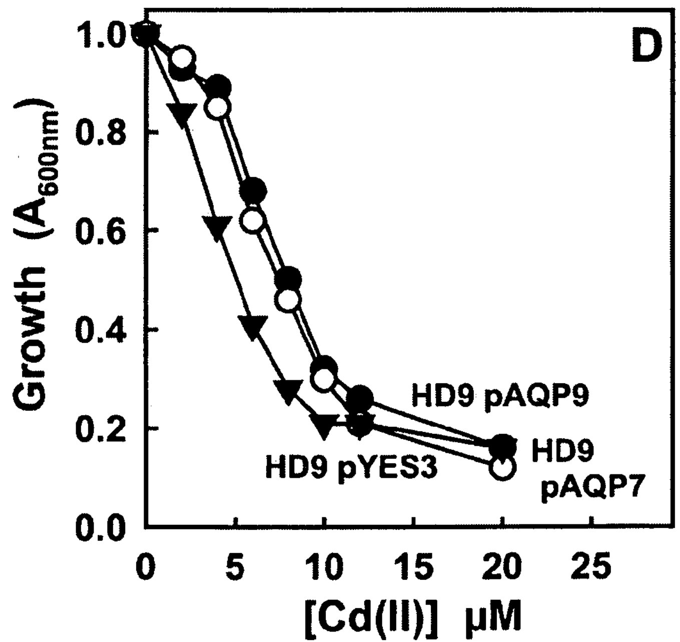

Compared to strain MG102, strain HD9 was resistant to arsenite (FIG. 3A). HD9 was also relatively resistant to antimonite (FIG. 3B) but not arsenate (FIG. 3C) or cadmium (FIG. 3D). This result is consistent with the proposal that Fps1p facilitates metalloid uptake in yeast (Wysocki et al., 2001). Strain HD9 was used as the host for analysis of AQP7 and AQP9 function. Expression of AQP9 reversed the arsenite (FIG. 3A) and antimonite (FIG. 3B) resistance phenotype of strain HD9. Reversal of the fps1Δ phenotype by expression of AQP9 from the GAL4 promoter required induction with galactose (FIG. 3A). AQP9 had no effect on sensitivity of strain HD9 to either arsenate (FIG. 3C) or cadmium (FIG. 3D). On the whole, these results clearly demonstrate that AQP9 can replace the function of Fps1p in trivalent metalloid sensitivity. Even though there was not enough AQP7 produced to be detected by Western blotting, it was possible that there was enough to complement the FSP1 deletion. However, introduction of AQP7 on a plasmid had no effect on resistance to either arsenite or antimonite.

Figure 4A:
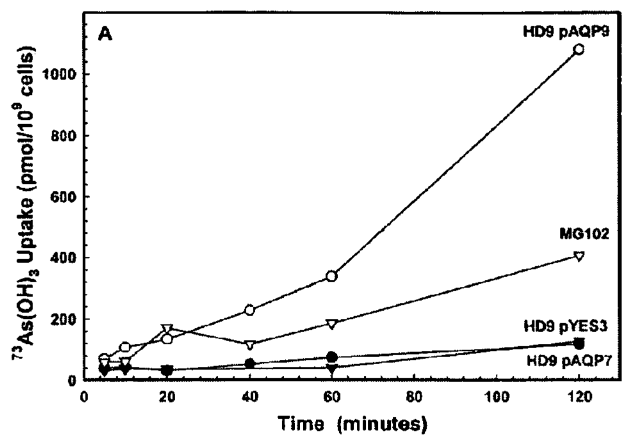
FIG. 4. AQP9 facilitates uptake of $^{73}As(OH)_3$ and $^{125}Sb(OH)_3$. (A) Transport of $^{73}As(OH)_3$. (B) Inhibition of $^{73}As(OH)_3$ uptake by glycerol. (C) Transport of $^{125}Sb(OH)_3$. Strains were: ●, HD9 pYES3; ○, HD9 pAQP9; ▼, HD9 pAQP7; ∇, MG102; and ■, HD9 pAQP9+0.2 M glycerol.
Figure 4B:
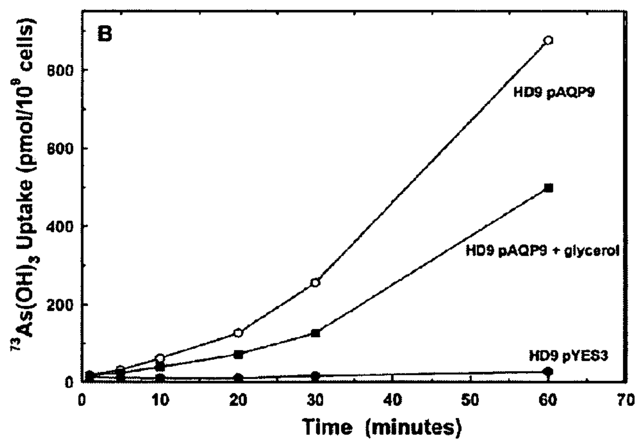

AQP9 Facilitates Uptake of $^{73}As(OH)_3$ and $^{125}Sb(OH)_3$ in *S. cerevisiae*. The ability of AQP9 to transport arsenite into yeast also was investigated. Strain MG102 lacks arsenite extrusion and, hence, accumulates arsenite (Ghosh et al., 1999). When FPS1 was deleted in this background, the rate of transport of $^{73}$As(III) was reduced (FIG. 4A). These results demonstrate that Fps1p facilitates uptake of $^{73}As(OH)_3$, which should be the predominant form at neutral pH. Because aquaporins are channels and do not exhibit energy-dependent concentration of solutes, the apparent accumulation probably reflects intracellular binding of arsenite. Cells expressing AQP9 accumulated more $^{73}As(OH)_3$ than the parental strain MG102. Transport of $^{73}$As(III) and $^{125}$Sb(III) (see below) consistently exhibited a lag, with increased intracellular arsenite observed at later time points, but the basis for this observation is unknown. Glycerol is the primary substrate of AQP9, so competition between glycerol and arsenite would be expected, and 0.2 M glycerol reduced the uptake of 5 μM arsenite (FIG. 4B). In growth assays, 0.2 M glycerol also produced a small reversal of the AQP9-related arsenite sensitivity (data not shown).

Figure 4C:
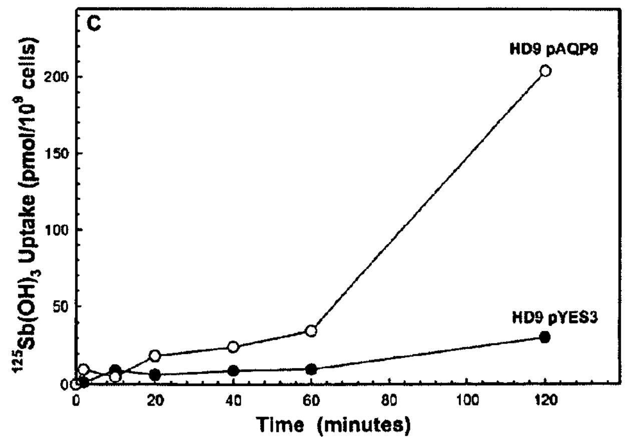

Transport of Sb(III) has been inferred from in vivo resistance assays, but direct measurement has not been possible because of the unavailability of radioactive antimony. For this study $^{125}$Sb was custom synthesized. Cells of the triple deletion fps1Δ acr3Δ ycf1Δ strain HD9 exhibited low rates of transport of $^{125}Sb(OH)_3$ compared to HD9 expressing AQP9, demonstrating that AQP9 facilitates transport of Sb(III) as well as As(III) (FIG. 4C).

Both AQP7 and AQP9 Facilitate $^{73}As(OH)_3$ Permeability in *Xenopus oocytes*.

Figure 5:
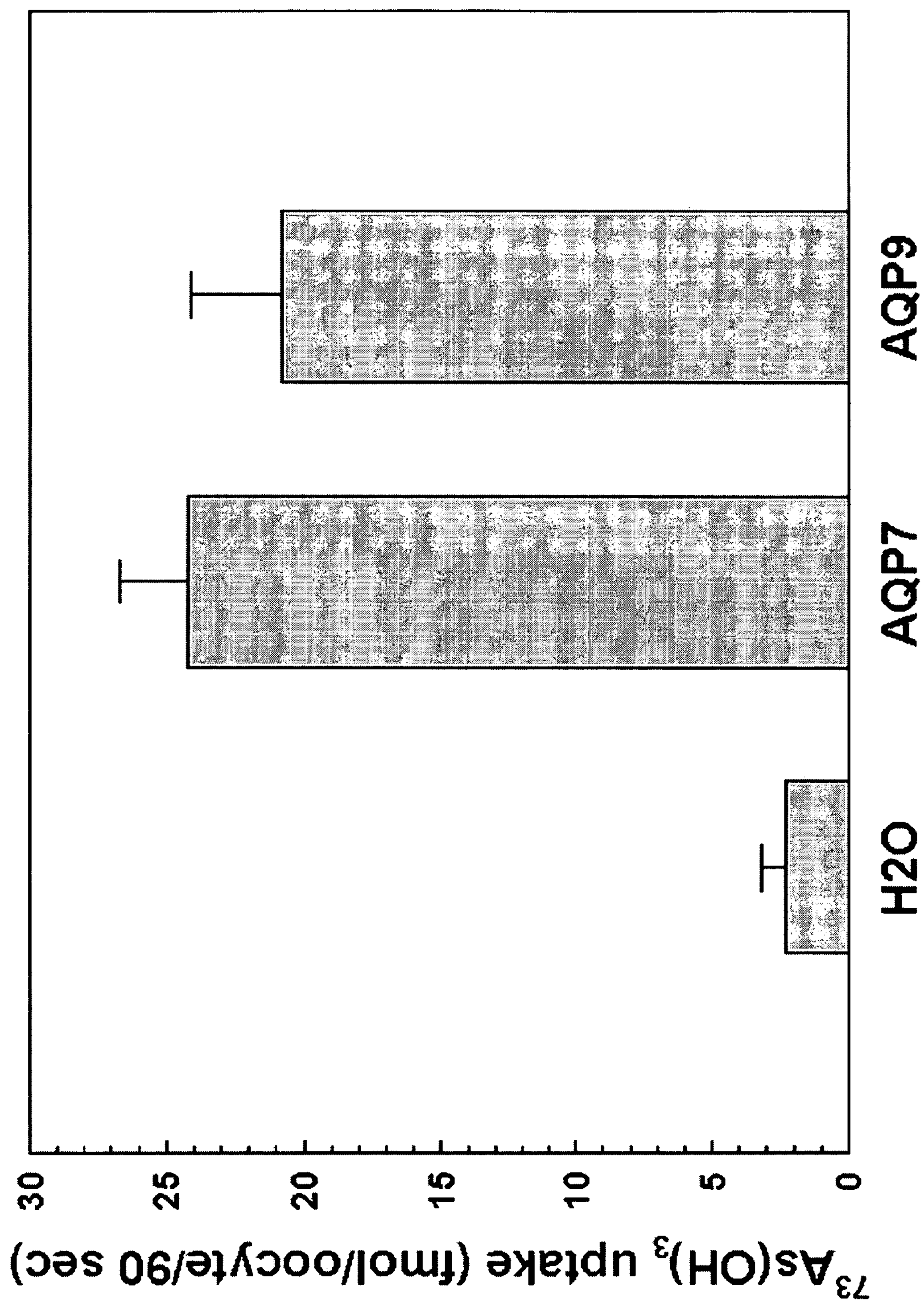
FIG. 5. $^{73}As(OH)_3$ permeability in *Xenopus oocytes* expressing AQP7 or AQP9. Oocyte transport of $^{73}As(OH)_3$ was assayed for 90 seconds as described in *Materials and Methods*. Each bar represents the average of three assays. Oocytes were injected with $H_2O$, AQP7 cRNA, or AQP9 cRNA.

Because AQP7 was not expressed in yeast, the ability of the aquaglyceroporins to increase arsenite permeability in *Xenopus oocytes* was examined. Water, AQP7, or AQP9 cRNA prepared in vitro was microinjected into *Xenopus oocytes*. Either aquaglyceroporin increased the uptake of $^{73}As(OH)_3$ approximately 10-fold (FIG. 5). These results suggest that both aquaglyceroporins can facilitate uptake of arsenite.

Discussion

Figure 6C:
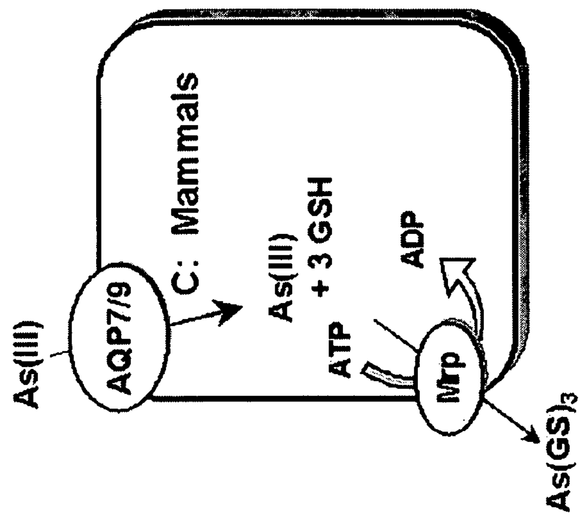
FIG. 6. Metalloid transporters in prokaryotes and eukaryotes. The model shows a comparison of arsenite transport pathways in *E. coli* (A), *S. cerevisiae* (B), and a generalized mammalian cell (C). In each of three, arsenite uptake is facilitated by an aquaglyceroporin: the bacterial GlpF, the yeast Fps1p, or the mammalian AQP7 or AQP9. In *E. coli*, arsenite is extruded from the cytosol by the ArsAB pump. In yeast, arsenite extrusion from the cytosol is catalyzed by Acr3p or into the vacuole by the ATP-coupled Ycf1p pump as $As(GS)_3$. In mammalian cells, various isoforms of the multidrug resistance associate protein (MRP), a Ycf1p homolog, pump out $As(GS)_3$.
Figure 6B:
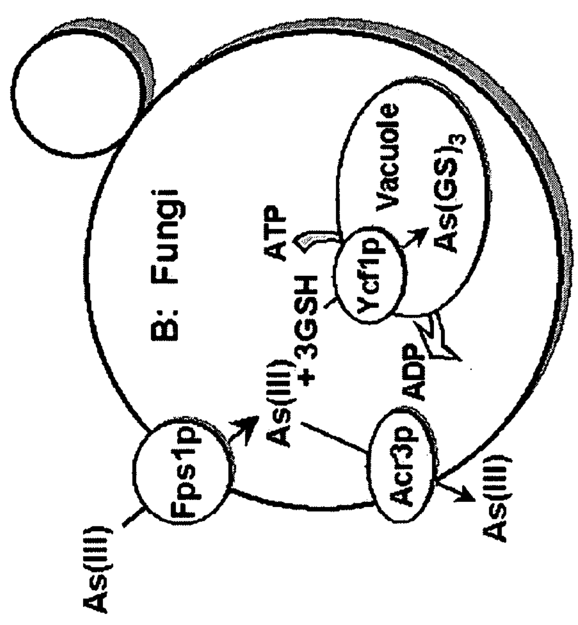
Figure 6A:
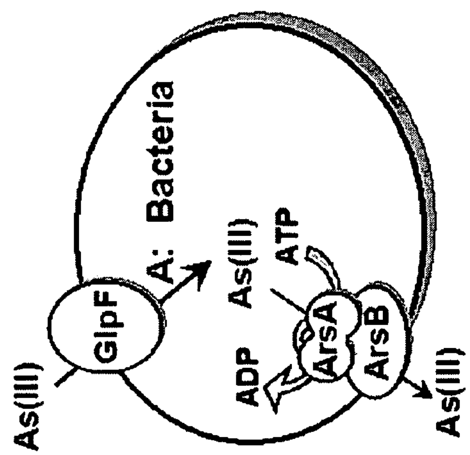

Aquaglyceroporins have been shown to facilitate metalloid uptake in both *E. coli* (Sanders et al., 1997) and *S. cerevisiae* (Wysocki et al., 2001). Without these transporters, cells are unusually resistant to arsenite and/or antimonite. The closest mammalian homologs to *E. coli* GlpF and yeast Fsp1p are AQP7 and AQP9. AQP9 can transport arsenite into yeast. AQP9 exhibits the broadest solute permeation, including carbamides, polyols, purines, and pyrimidines (Tsukaguchi et al., 1998). AQP7, which is expressed in testis (Ishibashi et al., 1997) and kidney (Nejsum et al., 2000) and has a narrower range of substrate specificity, transporting primarily glycerol and urea (Ishibashi et al., 1997), was not expressed in yeast. However, in *Xenopus laevis oocytes* AQP7 and AQP9 both increased arsenite permeability. These results indicate that both AQP7 and AQP9 may be routes of arsenite uptake into mammalian cells (FIG. 6).

The structure of aquaporin AQP1 (Murata et al., 2000; Sui et al., 2001) and aquaglyceroporin GlpF (Fu et al., 2000) have recently been determined at atomic resolution, and the spacing at the narrowest region of the pore (the aromatic/arginine ring) is significantly wider in the aquaglyceroporin. Molecular dynamics simulation may now reveal the permeation mechanism for metalloid transport by AQP7 and AQP9. Arsenite and antimonite are commonly considered oxyanions. Indeed, transport of arsenite by the bacterial ArsB carrier is driven by the membrane potential, suggesting anionic substrates (Dey and Rosen II; Kuroda et al., 1997). However the trivalent arsenic and antimony acids have pKa values of 9.2 and 11.8, respectively, so that at neutral pH they would be primarily present in solution as neutral species, $As(OH)_3$ or $Sb(OH)_3$.

Arsenic is classified as a carcinogen by the Environmental Protection Agency (Smith et al., 1992). Possible mechanisms of carcinogenesis include genetic instability resulting from inhibition of telomerase transcription (Chou et al., 2001) or by acting as a cocarcinogen to inhibit DNA repair (Rossman et al., 2001). Exposure to arsenic in drinking water is associated with increased risk of multiple cancers. According to the Natural Resources Defense Council, millions of Americans are consuming tap water every day that poses unacceptable cancer risks (as posted on the world wide web at nrdc.org/water/drinking/qarsenic.asp, Mar. 21, 2001). Over 56 million Americans in the 25 reporting states consumed water from systems containing arsenic at levels presenting a potentially fatal cancer risk. Based on reports by the U.S. National Research Council, the Environmental Protection Agency has amended the Safe Drinking Water Act to lower the standard for arsenic in drinking water from 50 to 10 μg/liter; however these standards are based on the assumption that individuals respond uniformly to arsenic (National Research Council, Subcommittee on Arsenic in Drinking Water (1999) *Arsenic in Drinking Water* (Nat'l. Acad. Press, Washington, D.C.)). Uniform arsenic uptake is very unlikely because levels of rat AQP9 expression in liver are known to exhibit wide variations because of age, gender, and nutritional status (Nicchia et al., 2001). Thus, humans would be expected to respond differently to arsenic in the water supply, and safety standards need to reflect the likelihood that some individual are at higher risk for toxicity.

Most of the epidemiological studies have been conducted in countries such as Taiwan, Bangladesh, and Chile, where arsenic exposure is endemic (Chappell et al., 1997; Mushak and Crocetti, 1995). Chronic effects of arsenic in the water supply include skin hyperpigmentation and keratoses of the hands and feet that frequently progress to skin cancers. In approximately 10% of these cases, exposure is associated with a very high incidence of lung, bladder, and other cancers. However, there is considerable variation in individual responses to arsenic. Some family members in arsenic-contaminated regions of Bangladesh exhibit acute arsenicosis and various forms of cancer, whereas other siblings show few or no adverse effects. Knowledge of the aquaglyceroporin status of these individuals, including DNA sequence and levels of expression, could illuminate reasons for these variations because individuals with increased expression of AQP7 or AQP9 may be more sensitive to environmental arsenic. Thus, the levels of AQP7 and/or AQP9 expression may be a biomarker for arsenic exposure.

AQP9 is primarily expressed in human lung, liver, and leukocytes (Tsukaguchi et al., 1999). Interestingly, liver is an organ where arsenite toxicity is found, and some malignancies of the leukocyte lineage respond to arsenite chemotherapy. A century ago, arsenic was recommended as an anti-leukemic agent; however its use was abandoned because of toxicity. More recently, arsenic trioxide, the anhydrous form of $As(OH)_3$ (Trisenox, Cell Therapeutics, Seattle) has been approved as a chemotherapeutic agent for the treatment of acute promyelocytic leukemia (Chappell et al., 1997; Mushak and Crocetti, 1995). AQP9 may be responsible for the chemotherapeutic effects of arsenite by facilitating diffusion of the agent into the leukemia cells. As has been found with most chemotherapeutic agents, resistance eventually arises with continued use (Dey and Rosen I), and arsenic trioxide resistance will eventually occur. Emergence of AQP9 negative clones of promyelocytic leukemia could signal the need to change therapy. Conversely, individuals with increased expression of AQP9 in liver may have altered sensitivity to arsenic trioxide.

The *Saccharomyces cerevisiae* FPS1 gene encodes a membrane protein homologous to the bacterial aquaglyceroporin GlpF and to mammalian aquaglyceroporins AQP7 and AQP9. Fps1p mediates glycerol uptake and glycerol efflux in response to hypoosmotic shock. Fps1p has been shown to facilitate uptake of the metalloids arsenite and antimonite, and the *Escherichia coli* homolog, GlpF, facilitates the uptake and sensitivity to metalloid salts. In this study, the ability of mammalian aquaglyceroporins AQP7 and AQP9 to substitute for the yeast Fps1p was examined.

The fps1Δ strain of *S. cerevisiae* exhibits increased tolerance to arsenite and antimonite compared to a wild-type strain. Introduction of a plasmid containing AQP9 reverses the metalloid tolerance of the deletion strain. AQP7 was not expressed in yeast. The fps1Δ cells exhibit reduced transport of $^{73}$As(III) or $^{125}$Sb(III), but uptake is enhanced by expression of AQP9. *Xenopus laevis oocytes* microinjected with either AQP7 or AQP9 cRNA exhibited increased transport of $^{73}$As(III).

REFERENCES

Adams et al., *Methods in Yeast Genetics: A Cold Spring Harbor Laboratory Course Manual*, Cold Spring Harbor Laboratory, Cold Spring Harbor, N.Y. (1998).

Adelman et al., DNA, 2, 183 (1983).

Aoyama. et al., *N-H Plant Journal*, 11, 605 (1997).

Barr et al., eds., *Yeast Genetic Engineering*, Butterworths, London (1989).

Bobrowicz et al., *Yeast*, 13, 819-828 (1997).

Borgnia et al., *Annu. Rev. Biochem*., 68, 425-458 (1999).

Bowman et al., *J. Biol. Chem*., 266, 7517-7523 (1991).

Bun-ya et al., *Curr. Genet*., 29, 344-351 (1996).

Chappell et al., *Environ. Health Perspect*., 105, 1060-1067 (1997).

Chou et al., *J. Clin. Invest*, 108, 1541-1547 (2001).

Cole et al., *Cancer Res*., 54, 5902-5910 (1994).

Crea et al., *Proc. Natl. Acad. Sci. U.S.A*., 75, 5765 (1978).

Dey et al., *Proc. Natl. Acad. Sci. U.S.A*., 93, 2192-2197 (1996).

Dey et al., *Mol. Biochem. Parasitol*., 6, 49-57 (1994).

Dey and Rosen, in Drug Transport in Antimicrobial and Anticancer Chemotherapy, ed. Georgopapadakou, N. H. (Dekker, New York), pp. 103-132 (1995) (Dey and Rosen I).

Dey and Rosen, *J. Bacteriol*., 177, 385-389 (1995) (Dey and Rosen II).

Déziel et al., *Biodegredation*, 10, 219-233 (1999).

Fauman et al., *Cell*, 93, 617-625 (1998).

Fu et al., *Science*, 290, 481-486, (2000).

Gatz, *Current Opinion in Biotechnology*, 7:168 (1996).

Gatz, C., *Annu. Rev. Plant Physiol. Plant Mol. Biol*., 48:89 (1997).

Ghosh et al., *Proc. Natl. Acad. Sci. U.S.A*., 96, 5001-5006 (1999).

Ghosh and Rosen, in "Heavy Metals in the Environment," ed. Sarkar & Dekker, New York (2002).

Gladysheva et al., *Biochemistry*, 33, 7288-7293 (1994).

Guarente et al., *Proc. Natl. Acad. Sci*., 79, 7410-7414 (1982).

Guthrie and Fink, *Meth. Enzymol*., 194, 1-993 (1991).

Haimeur et al., *Mol. Microbiol*., 34, 726-735 (1999).

Heller et al., *J. Bacteriol*., 144, 274-278 (1980).

Hofmann et al., *J. Mol. Biol*., 282, 195-208 (1998).

Ikuta et al., *Biotech*., 8:241 (1990).

Ishibashi et al., *J. Biol. Chem*., 272, 20782-20786 (1997).

Ito et al., *J. Bacteriol*., 153, 163-168 (1983).

Ji et al., *Biochemistry*, 33, 7294-7299 (1994).

Katz et al., *J. Gen. Microbiol*., 129:2703 (1983).

Laemmli, *Nature* (*London*), 227, 680-685 (1970).

Legare et al., *J. Biol. Chem*., 276, 26301-26307 (2001).

Luyten et al., *EMBO J*., 14, 1360-1371 (1995).

Li et al., *Proc. Natl. Acad. Sci. U.S.A*., 94, 42-47 (1997).

Li et al., *J. Biol. Chem*., 271, 6509-6517 (1996).

Liu et al., *Proc. Natl. Acad. Sci. U.S.A*., 99, 6053-6058 (2002).

Mobley and Rosen, *Proc. Natl. Acad. Sci. U.S.A*., 79, 6119-6122 (1982).

Mukhopadhyay et al., *Proc. Natl. Acad. Sci. U.S.A*., 93, 10383-10387 (1996).

Mukhopadhyay and Rosen, *FEMS Microbiol. Lett*., 168, 127-136 (1998).

Mukhopadhyay et al., *J. Biol. Chem*., 275, 21149-21157 (2000).

Murata et al., *Nature* (*London*) 407, 599-605 (2000).

Mushak and Crocetti, *Environ. Health Perspect*., 103, 684-689 (1995).

Nejsum et al., *Biochem. Biophys. Res. Commun*., 277, 164-170 (2000).

Nicchia et al., *J. Histochem. Cytochem*., 49, 1547-1556 (2001).

Niedz et al., *Plant Cell Reports*, 14: 403 (1995).

Ow et al., *Science*, 234:856 (1986).

Prasher et al., *Biochem. Biophys. Res. Comm*., 126:1259 (1985).

Preston et al., *Science*, 256, 385-387 (1992).

Reay and Asher, *Anal. Biochem*., 78, 557-560 (1977).

Rensing et al., *J. Bacteriol*., 181, 5891-5897 (1999).

Ritten and Scarborough, *J. Environ. Sci. Health*, A30, 333-357 (1995).
Rosen, *J. Basic Clin. Physiol. Pharmacol.*, 6, 251-263 (1995).
Rosen, *J. Biol. Inorg. Chem.*, 1, 273-277 (1996).
Rosen, In S. J. Higgins and D. P. Ballou (ed.), *Metalloproteins*, 34 Portland Press, Ltd., London (1998).
Rosen, *Trends Microbiol.*, 7, 207-212 (1999) (Rosen I).
Rosen, *Essays Biochem.*, 34, 1-15 (1999) (Rosen II).
Rossman et al., *Toxicol. Appl. Pharmacol.*, 176, 64-71 (2001).
Rothstein, *Methods Enzymol.*, 194, 169-270(1991).
Sambrook et al., eds., *Molecular Cloning, A Laboratory Manual*, Cold Spring Harbor Laboratory Press, Plainview, N.Y. (1989).
Sambrook and Russell, eds., *Molecular Cloning, A Laboratory Manual*, Cold Spring Harbor Laboratory, New York (3d ed. 2001).
Sanders et al., *J. Bacteriol.*, 179, 3365-3367 (1997).
Smith et al., *Environ. Health Perspect.*, 97, 259-267 (1992).
Soignet et al., *N. Engl. J. Med.*, 339, 1341-1348 (1998).
Sui et al., *Nature* (*London*), 414, 872-878 (2001).
Sutcliffe, *PNAS USA*, 75:3737 (1978).
Sweet et al., *J. Bacteriol.*, 172, 424-430 (1990).
Szczypka et al., *J. Biol. Chem.*, 269, 22853-22857 (1994).
Tamas and Wysocki, *Curr. Genet.*, 40, 2-12 (2001).
Tsukaguchi et al., *J. Biol. Chem.*, 273, 24737-24743 (1998).
Tsukaguchi et al., *Am. J. Physiol.*, 277, F685-F696 (1999).
Van Aelst et al., *EMBO J.*, 10, 2095-2104 (1991).
Vieira et al., *Methods Enzymol.*, 153, 3-11 (1987).
Waldman, *Dangerous Waters: All Agree Arsenic Kills. The Question is How Much it Takes to Do So*, The Wall Street Journal, Apr. 19, 2001 at A1, A8.
Wang et al., *Toxicol. Appl. Pharmacol.*, 137, 112-119 (1996).
Willsky and Malamy, *J. Bacteriol.*, 144, 356-365 (1980).
Wu et al., *J. Biol. Chem.*, 267, 12570-12576 (1992).
Wysocki et al., *J. Biol. Chem.*, 272, 30061-30066 (1997).
Wysocki et al., *Mol. Microbiol.*, 40, 1391-1401 (2001).
Xu et al., *J. Biochem.*, 123, 16-23 (1998).
Yanisch-Perron et al., *Gene*, 33, 103-119 (1985).
Zukowsky et al., *PNAS USA*, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified transgenic *Saccharomyces cerevisiae* yeast cell comprising:

(a) a disrupted ACR3 gene of said yeast cell, wherein the disruption results in a reduction of heavy metal extrusion in the transgenic *Saccharomyces cerevisiae* yeast cell as compared to a corresponding wild-type *Saccharomyces cerevisiae* yeast cell; and (b) a recombinant DNA sequence comprising a promoter operably linked to a nucleic acid molecule encoding yeast cadmium factor resistance protein Ycf1p, wherein the transgenic *Saccharomyces cerevisiae* yeast cell over-expresses Ycf1p as compared to a corresponding wild-type *Saccharomyces cerevisiae* yeast cell, such that the overexpression of Ycf1p and the reduction of heavy metal extrusion causes the transgenic *Saccharomyces cerevisiae* to have increased accumulation of at least one heavy metal from the cytosol into vacuoles relative to heavy metal accumulation from the cytosol into vacuoles in a corresponding *Saccharomyces cerevisiae* yeast cell with a disrupted ACR3 gene but not the recombinant DNA.

2. The trarisgenic *Saccharomyces cerevisiae* yeast cell of claim 1 wherein the ACR3 gene is disrupted by insertional inactivation.

3. The transgenic *Saccharomyces cerevisiae* yeast cell of claim 2 wherein the ACR3 gene is disrupted by homologous recombination of the ACR3 gene with a heterologous DNA sequence.

4. The transgenic Saccharomyces cerevisiae yeast cell of claim 1 wherein Ycf1p overexpression is inducible.

5. The transgenic *Saccharomyces cerevisiae* yeast cell of claim 1 wherein the heavy metal is selected from As(V), As(III), cadmium (Cd(II)), antimony (Sb (V), Sb(III)), mercury (Hg(II)), and lead (Pb(II)).

6. The transgenie *Saccharomyces cerevisiae* yeast cell of claim 5, wherein the heavy metal is As(V) or As(III).

7. The transgenic *Saccharomyces cerevisiae* yeast cell of claim 1 further comprising an isolated DNA sequence comprising a promoter operably linked to a second nucleic acid molecule comprising an ACR2 gene.

8. The transgenic *Saccharomyces cerevisiae* yeast cell yeast of claim 7 wherein Acr2p is overexpressed from the ACR2 gene in the transgenic *Saccharomyces cerevisiae* yeast cell as compared to a wild-type *Saccharomyces cerevisiae* yeast cell such the reduction of As(V) to As(III) in the transgenic *Saccharomyces cerevisiae* yeast cell is not a rate limiting step in the detoxification of arsenic in the transgenic *Saccharomyces cerevisiae* yeast cell.

9. The transgenic *Saccharomyces cerevisiae* yeast cell of claim 1, wherein the Acr3p disruption results in a reduction in As(III) extrusion.

10. The transgenic *Saccharomyces cerevisiae* yeast cell of claim 1, further comprising a second recombinant DNA sequence comprising a promoter operably linked to a nucleic acid molecule encoding an aquaglyceroporin, wherein the transgenic *Saccharomyces cerevisiae* yeast cell expresses the aquaglyceroporin so as to cause the transgenic *Saccharomyces cerevisiae* yeast cell to have enhanced metalloid uptake from the aqueous medium relative to a corresponding cell without the second recombinant DNA sequence.

11. The transgenic *Saccharomyces cerevisiae* yeast cell of claim 10, wherein the aquaglyceroporin is Fps1p, AQP7or AQP9.

12. The transgenic *Saccharomyces cerevisiae* yeast cell of claim 10, wherein the aquaglyceroporin is Fps1p or AQP9.

13. A method for bioremediation of water contaminated with a heavy metal comprising:

(a) contacting the water with a population of yeast cells of claim 1 contained within a bioreactor, wherein the cells reduce the amount of heavy metal in the water; and (b) monitoring the concentration of heavy metal in the water before and after the contact.

14. A bioreactor comprising a population of the yeast cells of claim 1.

15. The transgenic *Saccharomyces cerevisiae* yeast cell of claim 1, wherein the Acr3p disruption results in a reduction in arsenite extrusion.

16. The transgenic *Saccharomyces cerevisiae* yeast cell of claim 10, wherein the aquaglycoporin is AQP9.

17. The method of claim 13 wherein the Acr3p disruption in the transgenic *Saccharomyces cerevisiae* results in a reduction in arsenite extrusion.

18. The method of claim 13 wherein the transgenic *Saccharomyces cerevisiae* yeast cell further comprises a second recombinant DNA sequence comprising a promoter operably linked to a nucleic acid molecule encoding an aquaglyceroporin, wherein the transgenic *Saccharomyces cerevisiae* yeast cell expresses the aquaglyceroporin so as to cause the transgenic *Saccharomyces cerevisiae* yeast cell to have enhanced metalloid uptake from the aqueous medium relative to a corresponding cell without the second recombinant DNA sequence.

19. The method of claim 18 wherein the aquaglyceroporin is Fps1p or AQP9.

20. The method of claim 13 wherein the heavy metal is selected from As(V), As(III), cadmium (Cd(II)), antimony (Sb (V), Sb(III)), mercury (Hg(II)), and lead (Pb(II)).

21. The method of claim 13 wherein the heavy metal is As(V) or As(III).

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Saccharomyces cerevisiae

<400> SEQUENCE: 1

cgacataagc ttatcttgtc c                                    21


<210> SEQ ID NO 2
<211> LENGTH: 23
<212> TYPE: DNA
<213> ORGANISM: Saccharomyces cerevisiae

<400> SEQUENCE: 2

gtcatttgag agattcgtac agc                                  23


<210> SEQ ID NO 3
<211> LENGTH: 28
<212> TYPE: DNA
<213> ORGANISM: Artificial Sequence
<220> FEATURE:
<223> OTHER INFORMATION: A primer

<400> SEQUENCE: 3

agatctatgt cagaagatca aaaaagtg                             28


<210> SEQ ID NO 4
<211> LENGTH: 47
<212> TYPE: DNA
<213> ORGANISM: Artificial Sequence
<220> FEATURE:
<223> OTHER INFORMATION: A primer
```

-continued

<400> SEQUENCE: 4
gaattcattt ctattgttcc atatataata tggtttaagg atcctcg 47

<210> SEQ ID NO 5
<211> LENGTH: 20
<212> TYPE: DNA
<213> ORGANISM: Saccharomyces cerevisiae

<400> SEQUENCE: 5
atgagtaatc ctcaaaaagc 20

<210> SEQ ID NO 6
<211> LENGTH: 18
<212> TYPE: DNA
<213> ORGANISM: Saccharomyces cerevisiae

<400> SEQUENCE: 6
tcatgttacc ttcttagc 18

<210> SEQ ID NO 7
<211> LENGTH: 36
<212> TYPE: DNA
<213> ORGANISM: Mus musculus

<400> SEQUENCE: 7
ggggaattca gatctatggc ccccaggtct gtgctg 36

<210> SEQ ID NO 8
<211> LENGTH: 36
<212> TYPE: DNA
<213> ORGANISM: Mus musculus

<400> SEQUENCE: 8
ggggaattca gatctttaga agtgctctag aggcac 36

<210> SEQ ID NO 9
<211> LENGTH: 38
<212> TYPE: DNA
<213> ORGANISM: Ratus norvegicus

<400> SEQUENCE: 9
gggagatctg aattcatgcc ttctgagaag gacggtgc 38

<210> SEQ ID NO 10
<211> LENGTH: 37
<212> TYPE: DNA
<213> ORGANISM: Ratus norvegicus

<400> SEQUENCE: 10
gggagatctg aattcctaca tgatgacact gagctcg 37